US009878071B2

(12) United States Patent
Novak et al.

(10) Patent No.: US 9,878,071 B2
(45) Date of Patent: Jan. 30, 2018

(54) COLLAGEN COMPOSITIONS AND METHODS OF USE

(71) Applicant: Purdue Research Foundation, West Lafayette, IN (US)

(72) Inventors: Tyler Anthony Novak, Lafayette, IN (US); Kevin Blum, Lanesville, IN (US); Corey Philip Neu, West Lafayette, IN (US); Sherry L. Voytik-Harbin, Zionsville, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/515,680

(22) Filed: Oct. 16, 2014

(65) Prior Publication Data
US 2015/0105323 A1 Apr. 16, 2015

Related U.S. Application Data

(60) Provisional application No. 61/895,831, filed on Oct. 25, 2013, provisional application No. 61/891,761, filed on Oct. 16, 2013.

(51) Int. Cl.
*A61L 31/04* (2006.01)
*A61L 27/24* (2006.01)
*A61L 27/50* (2006.01)
*A61L 27/56* (2006.01)

(52) U.S. Cl.
CPC ............ *A61L 31/044* (2013.01); *A61L 27/24* (2013.01); *A61L 27/50* (2013.01); *A61L 27/56* (2013.01)

(58) Field of Classification Search
None
See application file for complete search history.

(56) References Cited

U.S. PATENT DOCUMENTS

| 3,949,073 | A | 4/1976 | Daniels et al. |
| 4,233,360 | A | 11/1980 | Luck et al. |
| 4,544,516 | A | 10/1985 | Hughes et al. |
| 4,582,640 | A | 4/1986 | Smestad et al. |
| 4,600,533 | A | 7/1986 | Chu et al. |
| 4,789,663 | A | 12/1988 | Wallace et al. |
| 4,902,508 | A | 2/1990 | Badylak et al. |
| 4,956,178 | A | 9/1990 | Badylak et al. |
| 5,163,955 | A | 11/1992 | Love et al. |
| 5,204,382 | A | 4/1993 | Wallace et al. |
| 5,275,826 | A | 1/1994 | Badylak et al. |
| 5,281,422 | A | 1/1994 | Badylak et al. |
| 5,420,248 | A | 5/1995 | Devictor et al. |
| 5,460,962 | A | 10/1995 | Kemp et al. |
| 5,554,389 | A | 9/1996 | Badylak et al. |
| 5,885,619 | A | 3/1999 | Patel et al. |
| 5,948,429 | A | 9/1999 | Bell et al. |
| 5,955,110 | A | 9/1999 | Patel et al. |
| 6,099,567 | A | 8/2000 | Badylak et al. |
| 6,187,047 | B1 | 2/2001 | Kwan et al. |
| 6,206,931 | B1 | 3/2001 | Cook et al. |
| 6,248,587 | B1 | 6/2001 | Rodgers et al. |
| 6,264,992 | B1 | 7/2001 | Voytik-Harbin et al. |
| 6,375,989 | B1 | 4/2002 | Badylak et al. |
| 6,384,196 | B1 | 5/2002 | Weis et al. |
| 6,444,229 | B2 | 9/2002 | Voytik-Harbin et al. |
| 6,497,875 | B1 | 12/2002 | Sorrell et al. |
| 6,576,265 | B1 | 6/2003 | Spievack |
| 6,586,493 | B1 | 7/2003 | Massia et al. |
| 6,592,623 | B1 | 7/2003 | Bowlin et al. |
| 6,592,794 | B1 | 7/2003 | Bachrach |
| 6,666,892 | B2 | 12/2003 | Hiles et al. |
| 6,793,939 | B2 | 9/2004 | Badylak |
| 6,893,812 | B2 | 5/2005 | Woltering et al. |
| 7,029,689 | B2 | 4/2006 | Berglund et al. |
| 8,084,055 | B2 | 12/2011 | Voytik-Harbin et al. |
| 8,241,905 | B2 | 8/2012 | Forgacs et al. |
| 8,343,758 | B2 | 1/2013 | Cheema et al. |
| 8,449,902 | B2 | 5/2013 | Brown et al. |
| 8,512,756 | B2 | 8/2013 | Voytik-Harbin et al. |
| 8,518,436 | B2 | 8/2013 | Voytik-Harbin et al. |
| 8,580,564 | B2 | 11/2013 | Brown et al. |
| 8,741,352 | B2 | 6/2014 | Hodde et al. |
| 8,785,389 | B2 | 7/2014 | Brown et al. |
| 9,101,693 | B2 | 8/2015 | Brown et al. |
| 2002/0076816 | A1 | 6/2002 | Dai et al. |
| 2002/0170120 | A1 | 11/2002 | Eckmayer et al. |
| 2002/0172705 | A1 | 11/2002 | Murphy et al. |

(Continued)

FOREIGN PATENT DOCUMENTS

| DE | 201 15 753 U1 | 1/2002 |
| EP | 0443094 | 8/1991 |
| EP | 1264878 | 12/2002 |
| EP | 1 270 672 A1 | 1/2003 |
| EP | 1 674 116 A2 | 6/2006 |
| GB | 2366736 | 3/2002 |
| JP | 07 074239 B | 8/1995 |
| WO | WO 94/03119 | 2/1994 |
| WO | WO 2001/023529 | 4/2001 |
| WO | WO 2001/045765 | 6/2001 |

(Continued)

OTHER PUBLICATIONS

Volpi et al., 1991, On the adaptive structures of the collagen fibrils of bone and cartilage, J Biomech, 24(Suppl 1): 67-77 (abstract only).*
Zhu et al., 2014, Designed composites for mimicking compressive mechanical properties of articular cartilage matrix, Journal of the Mechanical Behavior of Biomedical Materials, 36: 32-46.*

(Continued)

*Primary Examiner* — Amber D Steele
(74) *Attorney, Agent, or Firm* — Faegre Baker Daniels LLP

(57) ABSTRACT

The present disclosure provides an engineered collagen composition comprising collagen, wherein the collagen composition is compressed to form a gradient of at least one physical property. Methods of using and of manufacturing the engineered collagen compositions of the present disclosure are also provided.

30 Claims, 18 Drawing Sheets

(56) References Cited

U.S. PATENT DOCUMENTS

| | | | |
|---|---|---|---|
| 2004/0037813 A1 | 2/2004 | Simpson et al. | |
| 2004/0078076 A1 | 4/2004 | Badylak et al. | |
| 2004/0137616 A1 | 7/2004 | Isseroff et al. | |
| 2005/0014181 A1 | 1/2005 | Galis et al. | |
| 2005/0019419 A1 | 1/2005 | Badylak et al. | |
| 2005/0153442 A1 | 7/2005 | Katz et al. | |
| 2005/0226856 A1 | 10/2005 | Ahlfors | |
| 2005/0260748 A1 | 11/2005 | Chang et al. | |
| 2005/0266556 A1 | 12/2005 | Yoder et al. | |
| 2006/0147501 A1 | 7/2006 | Hillas et al. | |
| 2006/0165667 A1 | 7/2006 | Laughlin et al. | |
| 2006/0235511 A1 | 10/2006 | Osborne | |
| 2007/0026518 A1 | 2/2007 | Healy et al. | |
| 2007/0077652 A1 | 4/2007 | Peled et al. | |
| 2007/0190646 A1 | 8/2007 | Engler et al. | |
| 2007/0269476 A1 | 11/2007 | Voytik-Harbin et al. | |
| 2008/0025956 A1 | 1/2008 | Yoder et al. | |
| 2008/0107750 A1 | 5/2008 | Hodde et al. | |
| 2008/0181935 A1 | 7/2008 | Bhatia et al. | |
| 2008/0199441 A1 | 8/2008 | Peled | |
| 2008/0268052 A1 | 10/2008 | Voytik-Harbin et al. | |
| 2009/0011021 A1 | 1/2009 | Voytik-Harbin et al. | |
| 2009/0069893 A1 | 3/2009 | Paukshto et al. | |
| 2009/0175922 A1 | 7/2009 | Voytik-Harbin et al. | |
| 2009/0280180 A1 | 11/2009 | Voytik-Harbin et al. | |
| 2010/0183698 A1* | 7/2010 | Brown | A61L 27/24 424/423 |
| 2010/0330181 A1* | 12/2010 | Castiglione-Dodd | A61K 9/0024 424/484 |
| 2012/0027732 A1 | 2/2012 | Voytik-Harbin et al. | |
| 2012/0094376 A1 | 4/2012 | Voytik-Harbin et al. | |
| 2012/0115222 A1 | 5/2012 | Voytik-Harbin et al. | |
| 2012/0171768 A1* | 7/2012 | Voytik-Harbin | A61L 27/24 435/395 |

FOREIGN PATENT DOCUMENTS

| | | |
|---|---|---|
| WO | WO 2002/102237 | 12/2002 |
| WO | WO 2003/068287 | 8/2003 |
| WO | WO 2003/071991 | 9/2003 |
| WO | WO 03/087337 | 10/2003 |
| WO | WO 03/097694 | 11/2003 |
| WO | WO 04/028404 | 4/2004 |
| WO | WO 2004/060426 | 7/2004 |
| WO | WO 04/078120 | 9/2004 |
| WO | WO 2006/003442 | 1/2006 |
| WO | WO 2006/124946 | 11/2006 |
| WO | WO 2006/125025 | 11/2006 |
| WO | WO 2007/028079 | 3/2007 |
| WO | WO 2007/136634 | 11/2007 |
| WO | WO 2008/036393 | 3/2008 |
| WO | WO 2009/076441 | 6/2009 |
| WO | WO 2010/123928 | 10/2010 |
| WO | WO 2011/009054 | 1/2011 |

OTHER PUBLICATIONS

Mienaltowski et al., 2014, Structure, Physiology, and Biochemistry of Collagens, Advances in Experimental Medicine and Biology, 802: 5-29.*

Brown et al., 2005, Ultrarapid Engineering of Biomimetic Materials and Tissues:Fabrication of Nano- and Microstructures by Plastic Compression, Advanced Functional Materials, 15: 1762-1770.*

Abou-Neel et al., 2006, Use of multiple unconfined compression for fine control of collagen gel schaffold and mechanical properties, Soft Matter, 2: 986-992.*

"Basement Membrane" accessed online at http://en.wikipedia.org/wiki/Basement_membrane#Composition on Jun. 11, 2010.

"Extracellular Matrix" accessed at http://en.wikipedia.org/wiki/Extracellular_matrix on Jun. 11 2010.

Bell, Brett J. et al., "Cell Density and Extracellular Matrix (ECM) Microstructure Control Mechanical Behavior of Engineered Tissue Constructs", *2005 Summer Bioengineering conference*, (Jun. 22-26, 2005).

Bjornsson, S., "Simultaneous Preparation and Quantitation of Proteoglycans by Precipitation with Alcian Blue", Analytical Biochemistry, vol. 210, 1993, pp. 282-291.

Brennan and Davison, "Role of aldehydes in collagen fibrillogenesis in vitro," Biopolymers, vol. 19, 1980, Issue 10, p. 1861-1873.

Brightman et al., "Time-Lapse Confocal Reflection Microscopy of Collagen Fibrillogenesis and Extracellular Matrix Assembly In Vitro", *Biopolymers*, vol. 54, 222-234, (2000).

Callister, W. D, Jr., Materials Science and Engineering: an Introduction, $3^{rd}$ edition, New York, NY, John Wiley & Sons, Inc., 1994.

Chandrakasan et al. J. Biol. Chem., 1976, 251:6062-67.

Ciovacco et al., Bone, 2009, 44(1):80-86.

Comper, W. D., and A. Veis, "Characterization of Nuclei in in Vitro Collagen Fibril Formation", Biopolymers, vol. 16, 1977, pp. 2133-2142.

Compston, "Bone marrow and bone: a functional unit," Journal of Endocrinology, 173: 387-394, 2002.

Davis, et al., "Injectable Self-Assembling Peptide Nanofibers Create Intramyocardial Microenvironments for Endothelial Cells", *Circulation*, 111, 442-50, (Feb. 1, 2005).

Fulzele, S. V., P. M. Satturwar, A. K. Dorle, "Study of the Biodegradation and in Vivo Biocompatibility of Novel Biomaterials", European Journal of Pharmaceutical Sciences, vol. 20, 2003. pp. 53-61.

Gallop, P. M., and S. Seifter, "Preparation and Properties of Soluble Collagens", Soluble Collagens, 1963, pp. 635-641.

Gelman et al., "Collagen Fibril Formation in Vitro," J. Biol. Chem., 1979, 254(22): 11741-11745.

Gelman et al., "Collagen Fibril Formation," J. Biol. Chem., 1979, 254(1):180-186.

Griffey, S., N. D. Schwade, C. G. Wright, "Particulate Dermal Matrix as an Injectable Soft Tissue Replacement Material", J. Biomed. Mater. Res. vol. 58, 2001, pp. 10-15.

Hou, et al., "Radiolabeled Cell Distribution After Intramyocardial, Intracoronary, and Interstitial Retrograde Coronary Venous Delivery", *Circulation*, 112, 150-6, (Aug. 30, 2005).

Hunt, T. K., P. Twomey, B. Zederfeldt, and J. E. Dunphy, "Respiratory Gas Tensions and PH In Healing Wounds", American Journal of Surgery, vol. 114, 1967, pp. 302-307.

Ingram, D. A., et al., "Identification of a Novel Hierarchy of Endothelial Progenitor Cells Using Human Peripheral and Umbilical Cord Blood", Blood, 104, 2752-2760, (2004).

International Search Report and Written Opinion for PCT/US2006/018998 filed May 16, 2006.

International Search Report and Written Opinion dated Nov. 29, 2007 for PCT/US2006/019130.

International Search Report for International Application No. PCT/US07/020463, dated Feb. 21, 2008, 6 pgs.

International Search Report/Written Opinion for PCT/US2007/011681 dated Nov. 6, 2007.

Kacena et al., J. of Histotechnology, 2004, 27:119-130.

Knott et al., "Collagen Cross-Links in Mineralizing Tissues: A Review of Their Chemistry, Function, and Clinical Relevance," 1998, 22(3):181-187.

Kondo et al., "Biology of Hematopoietic Stem Cells and Progenitors: Implications for Clinical Application," Annu. Rev. Immunol., 2003, 21:759-806.

Korff et al., Jour. of Cell Science, vol. 112: 3249-3258 (1999).

Kreger et al., "Hyaluronan concentration within a 3D collagen matrix modulates matrix viscoelasticity, but not fibroblast response," Matrix Biol., 2009, 28(6):336-46.

Kreger, "Design of 3D Collagen Matrices for Cell Delivery and Guidance in Tissue Engineering," Thesis Submitted to the Faculty of Purdue University in Partial Fulfillment of the Requirements for the Degree of Doctor of Philosophy, May 2009, Purdue University.

Lin et al., "Comparison of Physical-Chemistry Properties of Type I Collagen from Different Species," *Food Chemistry*, 99(2): 244-251 (2005).

(56) References Cited

OTHER PUBLICATIONS

Malvern, *Introduction to the Mechanics of a Continuous Medium*. Upper Saddle River, NJ: Prentice-Hall, 1969.
Marotta, M., G. Martino, "Sensitive Spectrophotometric Method for the Quantitative Estimation of Collagen", Analytical Biochemistry, vol. 150, 1985, pp. 86-90.
Miller et al., "Preparation and Characterization of the Different Types of Collagen," *Methods in Enzymology*, 82: 33-64 (1982).
Miller, E. J., E. H. Epstein, Jr., and K. A. Piez, "Identification of Three Genetically Distinct Collagens by Cyanogen Bromide Cleavage of Insoluble Human Skin and Cartilage Collagen", Biochemical and Biophysical Research.
Na, "Monomer and Oligomer of Type I Collagen: Molecular Properties and Fibril Assembly," *Biochemistry*, 1989, 28(18):7161-7167.
Narmoneva et al., "Endothelial Cells Promote Cardiac Myocyte Survival and Spatial Reorganization", *Circulation*, 110, 962-968, (Aug. 24, 2004).
Nguyen et al., "Comparison of the Amino Acid Composition of Two Commercial Porcine Skins (Rind)," *Journal of Agricultural and Food Chemistry*, 34(3): 565-572 (1986).
Nielsen, T. B. and J. A. Reynolds, "Measurements of Molecular Weights by Gel Electrophoresis", Methods in Enzymology, vol. 48, Hirs and Temasheff, Eds., Academic Press, New York, 1978, pp. 3-10.
Orschell-Traycoff et al., Blood, 2000, 96:1380-1387.
Osborne, et al., "Investigation into the tensile properties of collagen/chondroitin-6-sulphate gels: the effect of crosslinking agents and diamines", *Medical & Biological Engineering & Computing*, vol. 36, 129-134, (1998).
Ozerdem, et al., "Physical Response of Collagen Gels to Tensile Strain", *Journal of Biomechanical Engineering*, vol. 117, 397-401, (Nov. 1995).
Pizzo et al., "Cell-Extracellular Matrix (ECM) Micro-Mechanical Behavior Depends on ECM Microstructure and Cell Type", *2005 Summer Bioengineering Conference*, (Jun. 22-26, 2005).
Pizzo et al., "Extracellular matrix (ECM) microstructural composition regulates local cell-ECM biomechanics and fundamental fibroblast behaviour: a multidimensional perspective", *J Appl Physiol*, 98: 1909-1921, (2005).
Pizzo et al., "Long-term Production of Choline Acetylatransferase in the CNS After Transplantation of Fibroblasts Modified with a Regulatable Vector", *Mol Brain Res*, 126, 1-13 (2004).
Rehman, et al., "Secretion of Angiogenic and Antiapoptotic Factors by Human Adipose Stromal Cells", *Circulation*, 109: 1292-8, (Mar. 16, 2004).
Reinlib, et al., "Cell Transplantation as Future Therapy for Cardiovascular Disease?", *Circulation*, 101: e182-e187, (2000).
Roeder B. A., K. Kokini, J. E. Sturgis, J. P. Robinson, S. L. Voytik-Harbin, "Tensile Mechanical Properties of Three-Dimensional Type 1 Collagen Extracellular Matrices with Varied Microstructure", J. Biomech. Eng., vol. 124, 2002. pp. 214-222.
Roeder et al., "Local, Three-Dimensional Strain Measurements Within Largely Deformed Extracellular Matrix Constructs", *J Biomech Eng*, 126, 699-708, (2004).
Scadden, "The stem cell niche as an entity of action," Nature, 441: 1075-1079, 2006.
Schechner et al., "In vivo formation of complex microvessels lined by human endothelial cells in an immunodeficient mouse," *PNAS*, Aug. 1, 2000, vol. 97, No. 16, 9191-9196.
Schilling, J. A., W. Joel, H. M. Shurley, "Wound Healing: A Comparative Study of the Histochemical Changes in Granulation Tissue Contained in Stainless Steel Wire Mesh and Polyvinyl Sponge Cylinders", Surgery, vol. 46, No. 4.
Shiozawa et al., "The bone marrow niche: habitat to hematopoietic and mesenchymal stem cells, and unwitting host to molecular parasites," Leukemia, 22(5): 941-950, 2008.
Sieminski et al., Expt. Cell Res., vol. 297, pp. 574-584 (2004).
Spradling et al., "Stem Cells Find Their Niche," Nature, 414: 98-104, 2001.

Strang, et al., *Linear Algebra and Its Applications*. 3rd edition. San Diego, CA: Academic Press, 1988.
Sykes, B., B. Puddle, M. Francis, and R. Smith, "The Estimation of Two Collagens from Human Dermis by Interrupted Gel Electrophoresis", Biochemical and Biophysical Research Communications, vol. 72, No. 4, 1976, pp. 1472-1480.
Veis, Arthur. et al., "Fundamentals of Interstitial; Collagen Self-Assembly", 1994, Extracellular Matrix Assembly and Structure, Academic Press, pp. 15-45.
Voytik-Harbin et al., "Application and Evaluation of the Alamarblue Assay for Cell Growth and Survival of Fibroblasts", *In Vitro Cell Dev Biol Anim*, 34, 239-246, (1998).
Voytik-Harbin et al., "Simultaneous Mechanical Loading and Confocal Reflection Microscopy for Three-Dimensional Microbiomechanical Analysis of Biomaterials and Tissue Constructs", *Microsc Microanal*, 9, 74-85, (2003).
Voytik-Harbin et al., Small Intestinal Submucosa: A Tissue-Derived Extracellular Matrix That Promotes Tissue-Specific Growth and Differentiation of Cells in Vitro, *Tissue Engineering*, 4, 2, 157-174, (1998).
Voytik-Harbin et al., "Three-Dimensional Imaging of Extracellular Matrix and Extracellular Matrix-Cell Interactions", *Methods in Cell Biology*, 63, 583-597. (2001).
Wess, Collagen fibrillar structure and hierarchies in P. Fratzl (ed.), Collagen: Structure and Mechanics, Springer Science + Business Media, LLC, New York, 2008, 53-60.
Yoder et al., "Redefining endothelial progenitor cells via clonal analysis and hematopoietic stem/progenitor cell principals," *Blood*, 2007, 109:1801-1809.
International Search Report and Written Opinion for PCT/US2008/086232, dated Jan. 16, 2009, 12 pages.
Bailey JL et al., "Collagen Oligomers Modulate Physical and Biological Properties of Three-Dimensional Self-Assembled Matrices," Biopolymers, 2010; 95(2): 77-93.
Na et al., "In Vitro Collagen Fibril Assembly in Glycerol Solution: Evidence for a Helical Cooperative Mechanism Involving Microfibrils," Biochemistry, 1986; 25: 958-966.
Na et al., "Mechanism of in Vitro Collagen Fibril Assembly," Journal of Biological Chemistry, 1986; 261(26): 12290-12299.
Voytik-Harbin et al., "Identification of Extractable Growth Factors from Small Intestine Submucosa," J Cell. Biochemistry, 1997; 67: 478-491.
Condell RA et al., "Analysis of Native Collagen Monomers and Oligomers by Size-Exclusion High-Performance Liquid Chromatography and its Application," *Analytical Biochemistry*, 1993; 212: 436-445.
"Density" form Merriam-Webster online, accessed on Feb. 1, 2011.
Brandner et al., "replicating the Hematopoietic Stem Cell Niche," Purdue University, BME Graduate Student Association Research Symposium, Poster Presentation, Jul. 16, 2009.
Whittington et al., "Collagen oligomers modulate physical and cell-instructive properties of polymerizable collagen matrices," Biomaterials Day Society for Biomaterials, Nov. 6, 2010 (PowerPoint presentation and poster).
Kreger et al., "Polymerization and matrix physical properties as important design considerations for soluble collagen formulations," 2010. Biopolymers, 93(8): 690-707.
Critser et al., "Collagen matrix physical properties modulate endothelial colony forming cell-derived vessels in vivo," 2010, Microvasc. Res., 80(1): 23-30.
Munakata, et al., Glycobiology, vol. 9, 1023-1027 (1999).
Kim, "Characterization of Acid-soluble Collagen from Pacific Whiting Surimi Processing Byproducts." J. Food Science, 2004, 69: C637-C642.
Billiar, Cellular and Biomolecular Mechanics and Mechanobiology, Amit Gefen, Ed., p. 210 (2011).
Ho et al., "Characterization of Collagen Isolation and Application of Collagen Gel as a Drug Carrier", J. of Controlled Release, vol. 44, pp. 103-112 (1997).
Liu, Asian-Aust J. Anim. Sci, 2001; 14(11):1638-1644.
Lynn et al., "Antigenicity and immunogenicity of collagen," J Biomed Mater Res, Part B: Appl Biomater, 2004; 71B: 343-354.

(56) References Cited

OTHER PUBLICATIONS

Taichman et al., "Human Osteoblasts Support Hematopoiesis through the Production of Granulocyte Colony-stimulating Factor," *Journal of Experimental Medicine*, 1994; 179:1677-1682.
TeBmar et al., "Hydrogels for tissue engineering," *Fundamentals of Tissue Engineering and Regenerative Medicine*, 2009; p. 495-517.
Koken, "About Collagen," Technical information, Support webpage, 2006.
Taqvi et al., "Influence of scaffold physical properties and stromal cell coculture on hematopoietic differentiation of mouse embryonic stem cells," *Biomaterials*, 2006; 24:6024-6031.
Engler et al., "Matrix elasticity directs stem cell lineage specification," *Cell*, 2006; 126:677-689.
Young, et al., "Adult Stem Cells." Anat. Record Pt. A: Disc. Mol. Cell. Evol. Biol. 276A:75-102 (2004).
Yang, et al., "The application of recombinant human collagen in tiussue engineering." *Biodrugs* 18:103-119 (2004).
Fischbach, et al., "Three-dimensional in vitro model of adipogenesis: coparison of culture conditions." *Tissue Engineering* 10:215-229 (2004).
Reinisch et al, "Humanized large-scale expanded endothelial colony-forming cells function in vitro and in vivo," *Blood*, 2009; 113:6716-6725.
Silver et al., "Collagen self-assembly and the development of tendon mechanical properties," *Journal of Biomechanics*, 2003; 36:1529-1553.
Product information: Collagen Solution—Type I from rat tail , Sigma, http://www.sigmaaldrich.com/etc/medialib/docs/Sigma/Datasheet/3/0867dat.Par.0001.File.tmp/c3867dat.pdf.
Gallagher D, "Stem cells being made from blood," available at www.bbc.co.uk/news/health-20539835.
Ingram D et al., "Vessel wall-derived endothelial cells rapidly proliferate because they contain a complete hierarchy of endothelial progenitor cells," *Blood*, 2005; 105(7):2783-6 (Epub Dec. 7, 2004).
Ingram D et al., "Unresolved questions, changing definitions, and novel paradigms for defining endothelial progenitor cells via clonal analysis and hematopoietic stem/progenitor cell principals," *Blood*, 2007; 109(5):1801-9 (Epub Oct. 19, 2006).
Prater DN et al.. "Working hypothesis to redefine endothelial progenitor cells," *Leukemia*, 2007; 21(6):1141-9 (Epub Mar. 29, 2007).
Case J et al., "Human CD34+AC133+VEGFR-2+ cells are not endothelial progenitor cells but distinct, primitive hematopoietic progenitors," *Exp Hematol.*, 2007; 35(7):1109-18.
Hirschi KK et al, "Assessing identify, phenotype, and fate of endothelial progenitor cells," *Arterioscler Thromb Vasc Biol*, 2008; 28(9):1584-95 (Epub Jul. 31, 2008).
Timmermans F et al., "Endothelial progenitor cells: identify defined?", *J Cell Mol Med*, 2009; 13(1):87-102.
Mund JA et al, "Endothelial progenitor cells and cardiovascular cell-based therapies," *Cytotherapy*, 2009; 11(2):103-13.
Chor Wing Tam et al. EWMA Journal, 2012; 12(2).
Boyd et al. Atlas and Text of Corneal Pathology and Surgery; 2011.
Stem Cell Differentiation (science and global issues/biology, cell biology), 2013.
Shimizu, "Fabrication of pulsatile cardiac tissue grafts using a novel 3-dimensional cell sheet manipulation technique and temperature-responsive cell culture surfaces," Circ Res., 2002, 90:e40-48.
Mizuno et al., "Osteogenesis by bone marrow stromal cells maintained on type 1 collagen matrix gels in vivo." Bone 20:101-107 (1997).
Young et al., "Use of meschymal stem cells in a collagen matrix for Achilles tendon repair." J. Ortopaedic Res. 16"406-413 (1998).
Vasiliev and Gelfand, Neoplastic and Normal Cells in Culture, Cambring University Press, p. 19, 1981.
"Stem Cells and the future os Regeerative Medicine" published by National Academy of Sciencies. p. 19, 2002.
McBeath et al., "Cell shape, cytoskeletal tension, and RhoA regulate stem cell lineage commitment," *Developmental Cell*, 2004; 6:483-495.
Engler et al., "Myotubes differentiate optimally on substrates with tissue-like stiffness: pathological implications for soft or stiff microenvironments," *Journal of Cell Biology*, 2004; 165:877-887.
Kong et al., "FRET measurements of cell-traction forces and nano-scale clustering of adhesion ligands varied by substrate stiffness," *PNAS*, 2005; 102:4300-4305.
Settleman, "Tension Precedes Commitment—Even for a Stem Cell," *Molecular Cell*, 2004; 14:148-150.
Engler et al., "Substrate elasticity directs adult mesenchymal stem cell differentiation," Abstract 783, The 37th Middle Atlantic Regional Meeting, May 2005.
Wang et al, Sheng Li Xue Bao, 2005, 57(2): 259-269; Abstract Only.
Williams et al, 1978, Journ Biol Chem, 253: 6578-6585.
Huang et al, 2005, Mechanisms and Dynamics of Mechanical Strengthening in Ligament-Equivalent Fibroblast-Populated Collagen Matrices, Annals of Biomedical Engineering, 21: 289-305.

\* cited by examiner

FIGURE 7
FIGURE 7A
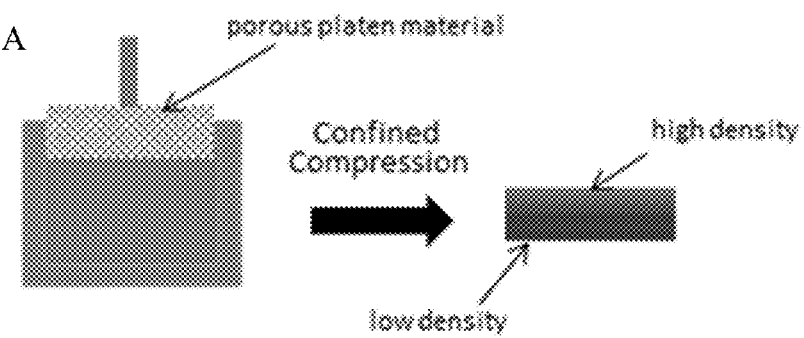
FIGURE 7B
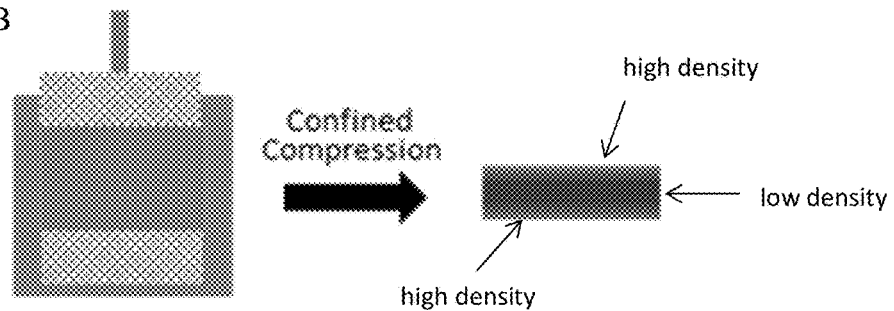

FIGURE 18
FIGURE 19
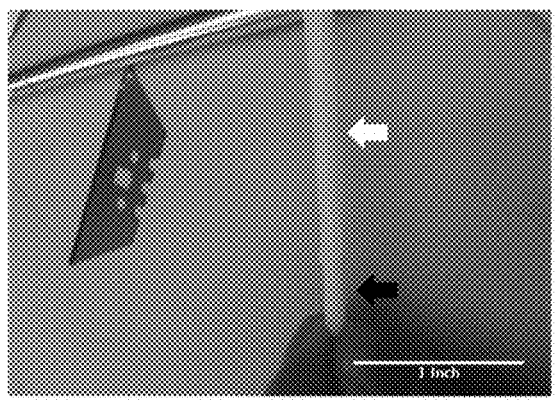
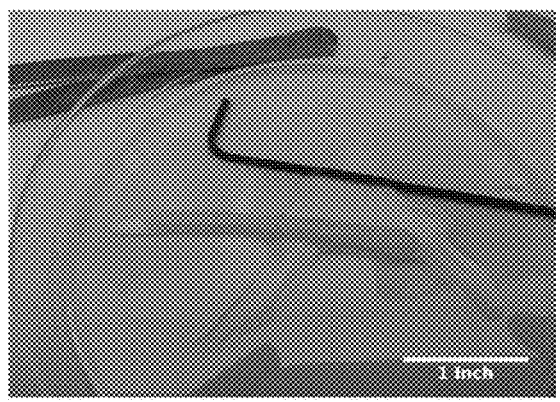

COLLAGEN COMPOSITIONS AND METHODS OF USE

CROSS REFERENCE TO RELATED APPLICATIONS

This application claims priority under 35 U.S.C §119(e) to U.S. Provisional Application Ser. No. 61/891,761, filed on Oct. 16, 2013, and to U.S. Provisional Application Ser. No. 61/895,831, filed on Oct. 25, 2013 the disclosures of both of which are herein incorporated by reference.

TECHNICAL FIELD

This disclosure relates to engineered collagen compositions comprising collagen, wherein the collagen composition is compressed to form a gradient of at least one physical property. This disclosure also relates to methods of manufacturing the engineered collagen compositions and methods of using the engineered collagen compositions.

BACKGROUND AND SUMMARY

The extracellular matrix (ECM) is known to provide scaffolding for cells while organizing the cells in three dimensions, as well as to provide essential information to regulate cell behavior. The field of tissue engineering strives to mimic both the form and function of these scaffolds to create compositions for optimal tissue repair and replacement. Collagen, and in particular Type I collagen, may be used in the field of tissue engineering due to its high availability in the body, conservation across tissues and species, biodegradability, and biocompatibility. Collagen is the most abundant molecule of the ECM and is responsible for the majority of the mechanical properties of several tissues. The in vivo form of collagen is a triple-helix center region capped at both ends by randomly organized telopeptides and contains natural molecular cross-links, which link the triple helices together into a branched network.

To date, collagen scaffolds known in the art have typically been utilized in the form of atelocollagen, which is characterized by the removal of telopeptides and of natural molecular cross-links, thus resulting in mechanical instability that limits its use as a larger sized implant. The instability of atelocollagen has led to a need for exogenous cross-linking strategies to return the collagen to a stronger, polymeric scaffold state. These cross-linking strategies, ranging from dehydrothermal and chemical treatments to copolymerization with other materials, have had varying success at increasing the stiffness of the collagen matrix, but undesirably affect the ability to mimic the in vivo structure and functionality of the collagen. Furthermore, the density of atelocollagen matrices has been limited by the starting collagen material (usually on the order of a maximum of 5-10 mg/mL), which is much less than the collagen concentration of 30-40 mg/mL found in connective tissues in vivo. This observation is of vital importance because matrix stiffness, a product of the collagen concentration, has been shown to directly impact the regulation of cell proliferation, migration, and differentiation.

Plastic compression has been performed on atelocollagen to force the fluid component out of the matrix, thus retaining the solid collagen component. These scaffolds have been shown to hold their shape and have higher mechanical properties compared to uncompressed atelocollagen gels. However, the compression processes used to create the atelocollagen compressed scaffolds are extreme processes, resulting in the excretion of nearly all of the fluid that can be removed from the scaffolds. As a result, the final material for the atelocollagen scaffold is often quite small, on the order of less than 100 µL of total volume following compression. In addition, it has been shown that the compression processes can reduce the cellular viability of the scaffolds and damage the natural matrix architecture that is essential to impact the regulation of cellular functions such as proliferation, migration, and differentiation.

Accordingly, there exists a need for alternative compression techniques to form collagen compositions that provide advantages in the field of tissue engineering. Surprisingly, the inventors have found that alternative collagen compression techniques can provide a gradient of a physical property within the composition, resulting in multiple regions within the collagen composition that can be utilized to regulate cellular functions.

The engineered collagen compositions of the present disclosure provide several advantages compared to those known in the art. First, the engineered collagen compositions of the present disclosure possess improved mechanical properties compared to those in the art. In particular, the engineered collagen compositions of the present disclosure are not as fragile and have improved strength. Furthermore, the engineered collagen compositions of the present disclosure have improved resistance to degradation.

Second, manufacturing the engineered collagen compositions of the present disclosure allows for induction of high level interfibril associations prior to compression of the compositions. This step allows for control of important mechanical properties prior to creation of the final compositions, and the controlled mechanical properties are retained following compression of the final compositions.

In addition, a multitude of mechanical properties can be "tuned" for the engineered collagen compositions of the present disclosure prior to compression. As a result, critical design features of collagen scaffolds can be optimized for purposes of predictably inducing desired cellular mechanisms and responses for repair and replacement in patients.

In one embodiment described herein, an engineered collagen composition is provided. The engineered collagen composition comprises collagen, wherein the collagen composition is compressed to form a gradient of at least one physical property.

In another embodiment, a method of treating a patient is provided. The method comprises the step of implanting the engineered collagen composition of the present disclosure into the patient.

In another embodiment, a method of manufacturing an engineered collagen composition is provided. The method comprises the step of compressing the collagen composition to form the gradient of at least one physical property.

Any of the embodiments described in the following clause list are considered to be part of the invention:

1. An engineered collagen composition comprising collagen, wherein the collagen composition is compressed to form a gradient of at least one physical property.

2. The engineered collagen composition of clause 1, wherein the collagen is solubilized from tissue.

3. The engineered collagen composition of clause 1 or clause 2, wherein the collagen composition is a medical graft.

4. The engineered collagen composition of any one of clauses 1 to 3, wherein the collagen is polymerizable collagen.

5. The engineered collagen composition of any one of clauses 1 to 4, wherein the collagen is Type I collagen.

6. The engineered collagen composition of any one of clauses 1 to 5, wherein the collagen is unnatural collagen.

7. The engineered collagen composition of any one of clauses 1 to 6, wherein the collagen is oligomeric collagen.

8. The engineered collagen composition of any one of clauses 1 to 6, wherein the collagen comprises oligomeric collagen.

9. The engineered collagen composition of any one of clauses 1 to 6, wherein the collagen consists essentially of oligomeric collagen.

10. The engineered collagen composition of any one of clauses 1 to 6, wherein the collagen consists of oligomeric collagen.

11. The engineered collagen composition of any one of clauses 1 to 6, wherein the collagen comprises monomeric collagen.

12. The engineered collagen composition of any one of clauses 1 to 6, wherein the collagen comprises atelocollagen.

13. The engineered collagen composition of any one of clauses 1 to 6, wherein the collagen comprises oligomeric collagen and atelocollagen.

14. The engineered collagen composition of any one of clauses 1 to 6, wherein the collagen comprises oligomeric collagen, monomeric collagen, and atelocollagen.

15. The engineered collagen composition of any one of clauses 1 to 14, wherein the collagen is selected from the group consisting of pig skin collagen, bovine collagen, and human collagen.

16. The engineered collagen composition of any one of clauses 1 to 14, wherein the collagen is synthetic collagen.

17. The engineered collagen composition of any one of clauses 1 to 15, wherein the collagen is recombinant collagen.

18. The engineered collagen composition of any one of clauses 1 to 17, wherein the collagen is present at a concentration of about 1 mg/ml to about 500 mg/ml.

19. The engineered collagen composition of any one of clauses 1 to 17, wherein the collagen is present at a concentration of about 1 mg/ml to about 400 mg/ml.

20. The engineered collagen composition of any one of clauses 1 to 17, wherein the collagen is present at a concentration of about 1 mg/ml to about 300 mg/ml.

21. The engineered collagen composition of any one of clauses 1 to 17, wherein the collagen is present at a concentration of about 1 mg/ml to about 200 mg/ml.

22. The engineered collagen composition of any one of clauses 1 to 17, wherein the collagen is present at a concentration of about 1 mg/ml to about 100 mg/ml.

23. The engineered collagen composition of any one of clauses 1 to 17, wherein the collagen is present at a concentration of about 2 mg/ml to about 5 mg/ml.

24. The engineered collagen composition of any one of clauses 1 to 17, wherein the collagen is present at a concentration of about 3.5 mg/ml.

25. The engineered collagen composition of any one of clauses 1 to 17, wherein the collagen is present at a concentration of about 4 mg/ml to about 10 mg/ml.

26. The engineered collagen composition of any one of clauses 1 to 17, wherein the collagen is present at a concentration of about 5 mg/ml.

27. The engineered collagen composition of any one of clauses 1 to 17, wherein the collagen is present at a concentration of about 10 mg/ml to about 20 mg/ml.

28. The engineered collagen composition of any one of clauses 1 to 17, wherein the collagen is present at a concentration of about 12 mg/ml.

29. The engineered collagen composition of any one of clauses 1 to 17, wherein the collagen is present at a concentration of about 20 mg/ml to about 30 mg/ml.

30. The engineered collagen composition of any one of clauses 1 to 17, wherein the collagen is present at a concentration of about 24 mg/ml.

31. The engineered collagen composition of any one of clauses 1 to 30, wherein the composition further comprises a polymer.

32. The engineered collagen composition of any one of clauses 1 to 31, wherein the composition further comprises a co-polymer.

33. The engineered collagen composition of any one of clauses 1 to 32, wherein the gradient is a compression-induced gradient.

34. The engineered collagen composition of any one of clauses 1 to 33, wherein the compression is a confined compression.

35. The engineered collagen composition of any one of clauses 1 to 33, wherein the compression is a variable compression.

36. The engineered collagen composition of any one of clauses 1 to 33, wherein the compression is a physical compression.

37. The engineered collagen composition of any one of clauses 1 to 33, wherein the compression is centrifugation.

38. The engineered collagen composition of any one of clauses 1 to 33, wherein the compression is ultracentrifugation.

39. The engineered collagen composition of any one of clauses 1 to 33, wherein the compression is evaporation.

40. The engineered collagen composition of any one of clauses 1 to 33, wherein the compression is aspiration.

41. The engineered collagen composition of clause 40, wherein the aspiration is vacuum aspiration.

42. The engineered collagen composition of any one of clauses 1 to 41, wherein the compression is a physical force from at least one direction.

43. The engineered collagen composition of any one of clauses 1 to 41, wherein the compression is a physical force from two or more directions.

44. The engineered collagen composition of any one of clauses 1 to 41, wherein the compression is a physical force from three or more directions.

45. The engineered collagen composition of any one of clauses 1 to 41, wherein the compression is a physical force from four or more directions.

46. The engineered collagen composition of any one of clauses 1 to 45, wherein the physical property is density.

47. The engineered collagen composition of any one of clauses 1 to 45, wherein the physical property is stiffness.

48. The engineered collagen composition of any one of clauses 1 to 45, wherein the physical property is fibril orientation.

49. The engineered collagen composition of any one of clauses 1 to 45, wherein the physical property is collagen microstructure.

50. The engineered collagen composition of any one of clauses 1 to 45, wherein the physical property is porosity.

51. The engineered collagen composition of any one of clauses 1 to 45, wherein the physical property is the ratio of collagen type.

52. The engineered collagen composition of any one of clauses 1 to 51, wherein the composition comprises at least two regions.

53. The engineered collagen composition of clause 52, wherein at least one region comprises a high fibril density, and wherein at least one other region comprises a low fibril density.

54. The engineered collagen composition of clause 52, wherein at least one region comprises a high stiffness, and wherein at least one other region comprises a low stiffness.

55. The engineered collagen composition of clause 52, wherein at least one region comprises a high porosity, and wherein at least one other region comprises a low porosity.

56. The engineered collagen composition of clause 52, wherein at least one region comprises an aligned fibril orientation, and wherein at least one other region comprises a random fibril orientation.

57. The engineered collagen composition of any one of clauses 1 to 56, wherein the composition further comprises cells.

58. The engineered collagen composition of clause 57, wherein the cells are stem cells.

59. The engineered collagen composition of any one of clauses 1 to 58, wherein the composition is a fibrous foam.

60. The engineered collagen composition of any one of clauses 1 to 58, wherein the composition is a hydrogel.

61. The engineered collagen composition of any one of clauses 1 to 60, wherein the composition is a collagen-fibril matrix.

62. The engineered collagen composition of any one of clauses 1 to 61, wherein the composition is a porous matrix.

63. The engineered collagen composition of any one of clauses 1 to 62, wherein the composition further comprises fluid.

64. The engineered collagen composition of clause 63, wherein the fluid percentage is present between about 25% to about 99%.

65. The engineered collagen composition of any one of clauses 1 to 64, wherein the composition is lyophilized.

66. A method of treating a patient comprising the step of implanting the engineered collagen composition of any one of the preceding clauses into the patient.

67. A method of manufacturing an engineered collagen composition of any one of the preceding clauses comprising the step of compressing the collagen composition to form the gradient of at least one physical property.

68. The method of clause 67, wherein the method comprises the step of polymerizing the collagen prior to compressing the collagen composition into a defined shape.

69. The method of clause 67 or clause 68, wherein the method comprises the step of tuning the physical property prior to compressing the collagen composition into a defined shape.

70. The method of any one of clauses 67 to 69, wherein the compression is modulated through patterned fluid removal.

71. The method of any one of clauses 67 to 69, wherein the compression is modulated through patterned air removal.

72. The method of any one of clauses 67 to 71, wherein the step of compressing removes fluid from the composition.

73. The method of any one of clauses 67 to 72, wherein the defined shape is a tube.

74. The method of any one of clauses 67 to 72, wherein the defined shape is a sheet.

75. The method of any one of clauses 67 to 72, wherein the defined shape is a sphere.

76. The method of any one of clauses 67 to 72, wherein the defined shape is a slab.

77. The method of any one of clauses 67 to 72, wherein the defined shape is a cylinder.

78. The method of any one of clauses 67 to 72, wherein the defined shape is a cone.

BRIEF DESCRIPTION OF THE DRAWINGS

FIGS. 7A and 7B show schematic representations of different compression formats that can be applied to yield different gradient compositions.

FIG. 18 shows the densified collagen-fibril tube (white arrow) prepared by vacuum aspiration of interstitial fluid component through porous polyethylene foam rod.

FIG. 19 shows the densified collagen-fibril tube after removal of porous polyethylene foam rod. The tube was able to support fluid flow through its lumen.

DETAILED DESCRIPTION OF THE ILLUSTRATIVE EMBODIMENTS

Figure 1:
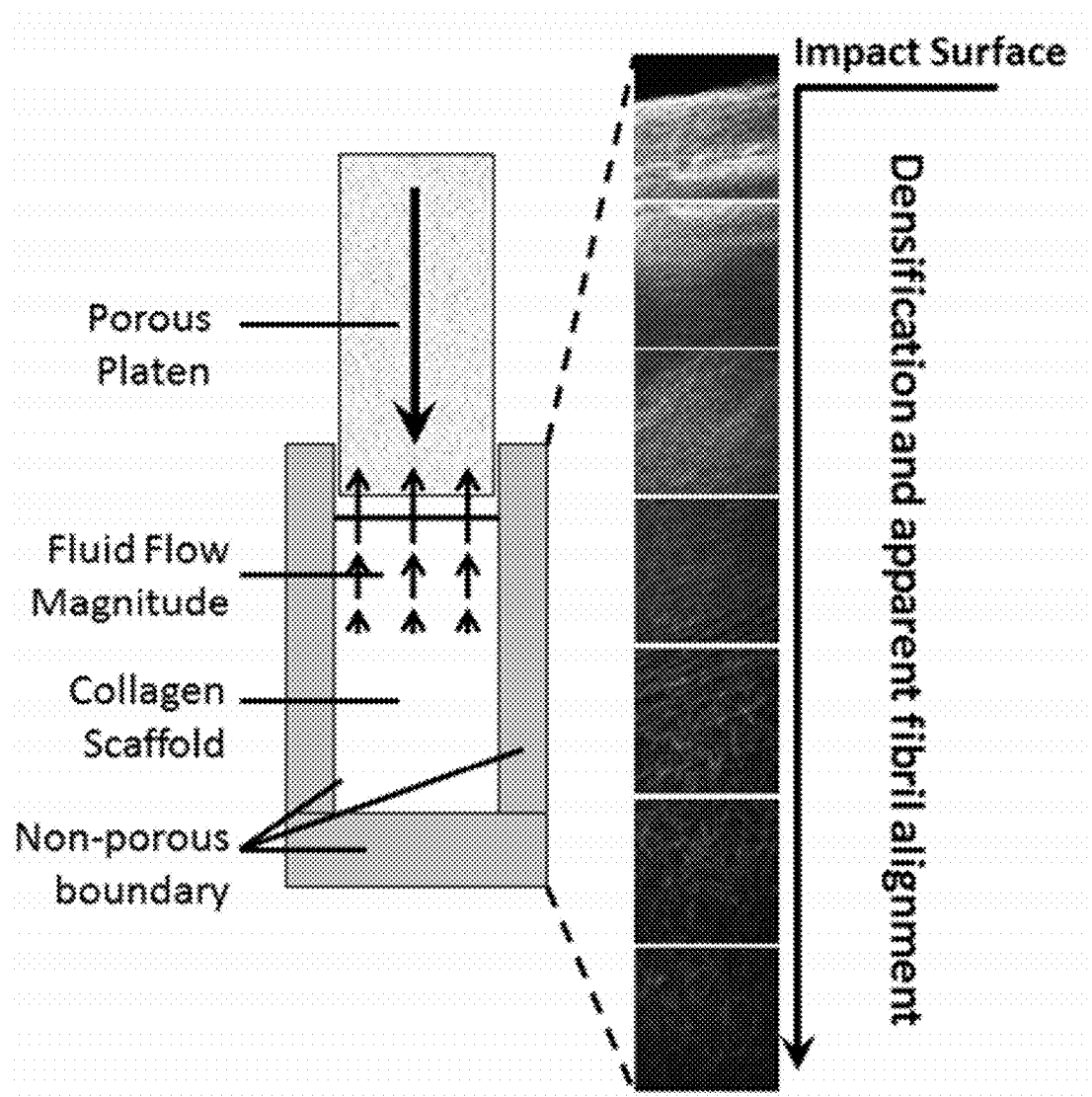
FIG. 1 shows collagen oligomers compressed via confined compression and then imaged under confocal microscopy. The intensity of the signal is indicative of the density of the local collagen matrix. As a result of confined compression, the matrix is heterogeneous, with high collagen density near the impacted surface which gradients to lower collagen density with depth toward the bottom (middle). Differences in collagen organization are also observed, where high density areas are seen to show fiber alignment and lower density areas are seen to show no apparent alignment.

For all of the embodiments described herein, any applicable combination of embodiments is contemplated. Any applicable combination of the embodiments described below is considered to be in accordance with the invention. Any combination of the embodiments described below with the embodiments described in the Summary of Invention section, including the clause list, is considered to be part of the invention.

In one embodiment described herein, an engineered collagen composition is provided. The engineered collagen composition comprises collagen, wherein the collagen composition is compressed to form a gradient of at least one physical property.

In another embodiment, a method of treating a patient is provided. The method comprises the step of implanting the engineered collagen composition of the present disclosure into the patient.

In another embodiment, a method of manufacturing an engineered collagen composition is provided. The method comprises the step of compressing the collagen composition to form the gradient of at least one physical property.

The engineered collagen compositions of the present disclosure comprise collagen. For example, an "engineered collagen composition" may refer to a collagen composition that may be polymerized, to form a collagen fibril containing matrix, under controlled conditions, wherein the controlled conditions include, but are not limited to, pH, phosphate concentration, temperature, buffer composition, ionic strength, and composition and concentration of the extracellular matrix components which includes both collagen and non-collagenous molecules.

The collagen compositions of the present disclosure are compressed to form a gradient of at least one physical property. As used herein, the term "compressed" refers to a reduction in size or an increase in density when a force is applied to the collagen composition. For example, compression can be achieved through various methods of applying force, such as, but not limited to, confined compression, variable compression, physical compression, centrifugation, ultracentrifugation, evaporation or aspiration.

Compression of the collagen compositions of the present disclosure forms a gradient of at least one physical property in the composition. According to the present disclosure, a "physical property" refers to any property of the collagen compositions, including structural, mechanical, chemical, and kinetic properties.

In some embodiments of the present disclosure, the collagen is solubilized from tissue. For example, the collagen can be prepared by utilizing acid-solubilized collagen and defined polymerization conditions that are controlled to yield three-dimensional collagen matrices with a range of controlled assembly kinetics (e.g., polymerization half-time), molecular compositions, and fibril microstructure-mechanical properties, for example, as described in U.S. patent application Ser. No. 11/435,635 (published Nov. 22, 2007, as Publication No. 2007-0269476 A1) and Ser. No. 11/903,326 (published Oct. 30, 2008, as Publication No. 2008-0268052), each incorporated herein by reference in its entirety. In other embodiments, the collagen is polymerizable collagen. In yet other embodiment, the collagen is Type I collagen.

In some embodiments, the engineered collagen composition is a medical graft. In other embodiments, the engineered collagen composition may be used in vitro. For example, in vitro use of the engineered collagen compositions of the present disclosure may be utilized for research purposes such as cell tissue culture, drug discovery, and drug toxicity testing.

In some embodiments, the collagen is unnatural collagen. As used herein, the phrase "unnatural collagen" refers to collagen that has been removed from a source tissue. Optionally, the unnatural collagen may be solubilized from the tissue source. In other embodiments, the collagen is synthetic collagen. In yet other embodiments, the collagen is recombinant collagen.

In one aspect, unnatural collagen or collagen components can be used and can be obtained from a number of sources, including for example, porcine skin, to construct the collagen compositions described herein. Suitable tissues useful as a collagen-containing source material for isolating collagen or collagen components to make the collagen compositions described herein are submucosa tissues or any other extracellular matrix-containing tissues of a warm-blooded vertebrate. Suitable methods of preparing submucosa tissues are described in U.S. Pat. Nos. 4,902,508; 5,281,422; and 5,275,826, each incorporated herein by reference. Extracellular matrix material-containing tissues other than submucosa tissue may be used to obtain collagen in accordance with the methods and compositions described herein. Methods of preparing other extracellular matrix material-derived tissues for use in obtaining purified collagen or partially purified extracellular matrix components are known to those skilled in the art. For example, see U.S. Pat. No. 5,163,955 (pericardial tissue); U.S. Pat. No. 5,554,389 (urinary bladder submucosa tissue); U.S. Pat. No. 6,099,567 (stomach submucosa tissue); U.S. Pat. No. 6,576,265 (extracellular matrix tissues generally); U.S. Pat. No. 6,793,939 (liver basement membrane tissues); and U.S. patent application publication no. US-2005-0019419-A1 (liver basement membrane tissues); and international publication no. WO 2001/45765 (extracellular matrix tissues generally), each incorporated herein by reference. In various other embodiments, the collagen-containing source material can be selected from the group consisting of placental tissue, ovarian tissue, uterine tissue, animal tail tissue, and skin tissue. In some embodiments, the collagen is selected from the group consisting of pig skin collagen, bovine collagen, and human collagen. Any suitable extracellular matrix-containing tissue can be used as a collagen-containing source material to isolate purified collagen or partially purified extracellular matrix components.

An illustrative preparation method for preparing submucosa tissues as a source of purified collagen or partially purified extracellular matrix components is described in U.S. Pat. No. 4,902,508, the disclosure of which is incorporated herein by reference. In one embodiment, a segment of vertebrate intestine, for example, preferably harvested from porcine, ovine or bovine species, but not excluding other species, is subjected to abrasion using a longitudinal wiping motion to remove cells or cell-removal is accomplished by hypotonic or hypertonic lysis. In one embodiment, the submucosa tissue is rinsed under hypotonic conditions, such as with water or with saline under hypotonic conditions and is optionally sterilized. In another illustrative embodiment, such compositions can be prepared by mechanically removing the luminal portion of the tunica mucosa and the external muscle layers and/or lysing resident cells with hypotonic or hypertonic washes, such as with water or saline. In these embodiments, the submucosa tissue can be stored in a hydrated or dehydrated state prior to isolation of the purified collagen or partially purified extracellular matrix components. In various aspects, the submucosa tissue can comprise any delamination embodiment, including the tunica submucosa delaminated from both the tunica muscularis and at least the luminal portion of the tunica mucosa of a warm-blooded vertebrate.

In some embodiments, the collagen is oligomeric collagen. The presence of oligomeric collagen enhances the self-assembly potential by increasing the assembly rate and by yielding collagen compositions with distinct fibril microstructures and increased mechanical integrity (e.g., stiffness). In some embodiments, the collagen comprises oligomeric collagen. In other embodiments, the collagen consists essentially of oligomeric collagen. In yet other embodiments, the collagen consists of oligomeric collagen.

In some embodiments, the collagen is monomeric collagen. In some embodiments, the collagen is atelocollagen. As used herein, the term "atelocollagen" refers to collagen that is treated in vitro with pepsin or another suitable protease or agent to eliminate or substantially reduce telopeptide regions which contain intermolecular cross-linking sites. In other embodiments, the monomeric collagen is telocollagen. As used herein, the term "telocollagen" refers to acid solubilized collagen that retains its telopeptide ends.

In certain embodiments, the collagen comprises oligomeric collagen and atelocollagen. In other embodiments, the collagen comprises oligomeric collagen, monomeric collagen, and atelocollagen. The amounts of oligomeric collagen, monomeric collagen, and/or atelocollagen may be formulated in the collagen compositions to advantageously maximize the stiffness, strength, fluid and mass transport, proteolytic degradation or compatibility of the engineered collagen compositions.

In any of the embodiments described herein, the collagen compositions can have a predetermined percentage of collagen oligomers. In various embodiments, the predetermined percentage of collagen oligomers can be about 0.5% to about 100%, about 30% to about 100%, about 40% to about 100%, about 50% to about 100%, about 60% to about 100%, about 70% to about 100%, about 80% to about 100%, about 90% to about 100%, about 95% to about 100%, or about 100%. In yet another embodiment, the collagen oligomers are obtained from a collagen-containing source material enriched with collagen oligomers (e.g., pig skin).

In any of the embodiments described herein, the engineered collagen matrices can have an oligomer content quantified by average polymer molecular weight (AMW). As described herein, modulation of AMW can affect polymerization kinetics, fibril microstructure, molecular properties, and fibril architecture of the matrices, for example, interfibril branching, pore size, and mechanical integrity (e.g., matrix stiffness). In another embodiment, the oligomer content of the purified collagen, as quantified by average polymer molecular weight, positively correlates with matrix stiffness.

In some embodiments, the collagen is thermoreversible collagen. As used herein "thermoreversible collagen" means collagen that can reversibly transition between solution and matrix phases in response to temperature modulation between 4° C. and 37° C. or temperature modulation between any other temperatures that cause reversible matrix to solution transitions.

In some embodiments, the collagen is reduced collagen. As used herein "reduced collagen" means collagen that is reduced in vitro to eliminate or substantially reduce reactive aldehydes. For example, collagen may be reduced in vitro by treatment of collagen with a reducing agent (e.g., sodium borohydride).

In some embodiments, the collagen is oligomer 260 collagen. As used herein "oligomer 260 collagen" is a collagen preparation made (e.g., from porcine skin), by procedures resulting in isolation of oligomers, where the collagen preparation has a prominent band at molecular weight 260, where the band is not prominent or is lacking in corresponding monomer preparations. The presence of the band can be determined by SDS polyacrylamide gel electrophoresis. Oligomer 260 collagen is further described U.S. patent application Ser. No. 13/192,276 (published Feb. 2, 2012, as Publication No. 2012-0027732 A1), incorporated herein by reference.

The concentration of collagen present in the compositions used to make the various embodiments of the present disclosure may vary. In some embodiments, the collagen is present at a concentration of about 1 mg/ml to about 500 mg/ml. In other embodiments, the collagen is present at a concentration of about 1 mg/ml to about 400 mg/ml. In yet other embodiments, the collagen is present at a concentration of about 1 mg/ml to about 300 mg/ml. In some embodiments, the collagen is present at a concentration of about 1 mg/ml to about 200 mg/ml. In other embodiments, the collagen is present at a concentration of about 1 mg/ml to about 100 mg/ml. In yet other embodiments, the collagen is present at a concentration of about 2 mg/ml to about 5 mg/ml. In some embodiments, the collagen is present at a concentration of about 3.5 mg/ml. In other embodiments, the collagen is present at a concentration of about 4 mg/ml to about 10 mg/ml. In yet other embodiments, the collagen is present at a concentration of about 5 mg/ml. In some embodiments, the collagen is present at a concentration of about 10 mg/ml to about 20 mg/ml. In other embodiments, the collagen is present at a concentration of about 12 mg/ml. In yet other embodiments, the collagen is present at a concentration of about 20 mg/ml to about 30 mg/ml. In some embodiments, the collagen is present at a concentration of about 24 mg/ml. In some embodiments, the collagen is present at a concentration of about 500 mg/ml. In other embodiments, the collagen is present at a concentration of about 400 mg/ml. In yet other embodiments, the collagen is present at a concentration of about 300 mg/ml. In other embodiments, the collagen is present at a concentration of about 200 mg/ml. In yet other embodiments, the collagen is present at a concentration of about 100 mg/ml. In other embodiments, the collagen is present at a concentration of about 75 mg/ml. In yet other embodiments, the collagen is present at a concentration of about 50 mg/ml.

In some embodiments, the composition further comprises a polymer. As used herein, the term "polymer" refers to a molecule consisting of individual chemical moieties, which may be the same or different, but are preferably the same, that are joined together. As used herein, the term "polymer" refers to individual chemical moieties that are joined end-to-end to form a linear molecule, as well as individual chemical moieties joined together in the form of a branched (e.g., a "multi-arm" or "star-shaped") structure. In other embodiments, the composition further comprises a co-polymer. As used herein, the term "co-polymer" refers to a polymer derived from more than one species of monomer, including copolymers that may be obtained by copolymerization of two monomer species, those that may be obtained from three monomers species ("terpolymers"), those that may be obtained from four monomers species ("quaterpolymers"), etc.

In certain embodiments, the gradient is a compression-induced gradient. As used herein, the phrase "compression-induced gradient" refers to a gradient in the collagen composition that is provided as a result of the compression to which the collagen composition is subjected.

In some embodiments, the compression is a confined compression. As used herein, the phrase "confined compression" refers to confinement of the collagen as it undergoes compression.

In other embodiments, the compression is a variable compression. As used herein, the phrase "variable compression" refers to compression of collagen by applying force in a non-linear fashion.

In yet other embodiments, the compression is a physical compression. As used herein, the phrase "physical compression" refers to compression of collagen by applying force by physical means.

In some embodiments, the compression is centrifugation. In other embodiments, the compression is ultracentrifugation. In yet other embodiments, the compression is evaporation. In some embodiments, the compression is aspiration. In certain embodiments, the aspiration is vacuum aspiration. In select embodiments, the compression is not plastic compression because such plastic compression may be an extreme process in which nearly all of the fluid removable from collagen compositions is excreted, and can reduce the cellular viability of the scaffolds and damage the natural matrix architecture.

Figure 6:
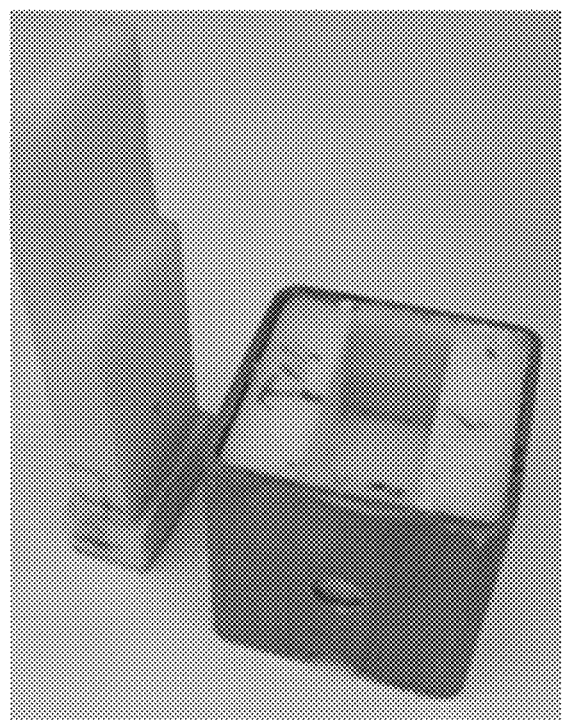
FIG. 6 shows a sample mold used for preparation and confined compression of collagen compositions. Sides and bottom of the mold were prepared from solid delrin and edges sealed with silicon epoxy, and the sample well measures 2 cm×4 cm×2.54 cm (L×W×D).

For embodiments in which the compression is a physical compression, the physical compression can be performed in a chamber comprising an adjustable mold and platen (see, for example, FIG. 6). Typically, collagen may be inserted into the mold and then subjected to compression.

Furthermore, the physical compression can be varied depending on the placement of the porous platen within the mold. For example, the mold may be adjustable so that porous polyethylene is positioned as part of the platen and/or along the walls or bottom of the sample mold. The location of the porous polyethylene can define the resultant material gradient in the collagen composition. In some embodiments, the compression is a physical force from at least one direction. In other embodiments, the compression is a physical force from two or more directions. In yet other embodiments, the compression is a physical force from three or more directions. In some embodiments, the compression is a physical force from four or more directions.

Pursuant to the present disclosure, the collagen compositions as herein described may be made under controlled conditions to obtain particular physical properties. For example, the collagen compositions may have desired collagen fibril density, pore size (fibril-fibril branching), elastic modulus, tensile strain, tensile stress, linear modulus, compressive modulus, loss modulus, fibril area fraction, fibril volume fraction, collagen concentration, cell seeding density, shear storage modulus (G' or elastic (solid-like) behavior), and phase angle delta ($\delta$ or the measure of the fluid (viscous)—to solid (elastic)—like behavior; $\delta$ equals 0° for Hookean solid and 90° for Newtonian fluid).

As used herein, a "modulus" can be an elastic or linear modulus (defined by the slope of the linear region of the stress-strain curve obtained using conventional mechanical testing protocols; i.e., stiffness), a compressive modulus, a loss modulus, or a shear storage modulus (e.g., a storage modulus). These terms are well-known to those skilled in the art.

As used herein, a "fibril volume fraction" (i.e., fibril density) is defined as the percent area of the total area occupied by fibrils in three dimensions.

As used herein, tensile or compressive stress "$\sigma$" is the force carried per unit of area and is expressed by the equation:

$$\sigma = \frac{P}{A} = \frac{P}{ab}$$

where
  s=stress
  P=force
  A=cross-sectional area.
  a=width
  h=height

The force (P) produces stresses normal (i.e., perpendicular) to the cross section of the part (e.g., if the stress tends to lengthen the part, it is called tensile stress, and if the stress tends to shorten the part, it is called compressive stress).

As used herein, "tensile strain" is the strain caused by bending and/or stretching a material.

In any embodiment described herein, the fibril volume fraction of the collagen composition is about 1% to about 60%. In various embodiments, the collagen composition can contain fibrils with specific characteristics, for example, a fibril volume fraction (i.e., density) of about 2% to about 60%, about 2% to about 40%, about 5% to about 60%, about 15% to about 60%, about 2% to about 30%, about 5% to about 30%, about 15% to about 30%, or about 20% to about 30%.

In any of the illustrative embodiments described herein, the collagen composition can contain fibrils with specific characteristics, including, but not limited to, a modulus (e.g., a compressive modulus, loss modulus, or a storage modulus) of about 10 Pa to about 3200 Pa, about 10 Pa to about 700 Pa, about 10 Pa to about 300 Pa, about 10 Pa to about 200 Pa, about 10 Pa to about 100 Pa, about 500 Pa to about 2000 Pa, about 700 Pa to about 1500 Pa, about 700 Pa to about 900 Pa, or about 800 Pa.

In any of the embodiments described herein, the collagen composition can contain fibrils with specific characteristics, including, but not limited to, a phase angle delta ($\delta$) of about 0° to about 12°, about 0° to about 5°, about 1° to about 5°, about 4° to about 12°, about 5° to about 7°, about 8° to about 10°, and about 5° to about 10°.

In any of the illustrative embodiments described herein, qualitative and quantitative microstructural characteristics of the collagen compositions can be determined by environmental or cryostage scanning electron microscopy, transmission electron microscopy, confocal microscopy, second harmonic generation multi-photon microscopy. In another embodiment, tensile, compressive and viscoelastic properties can be determined by rheometry or tensile testing. All of these methods are known in the art or are further described in U.S. patent application Ser. No. 11/435,635 (published Nov. 22, 2007, as Publication No. 2007-0269476 A1), U.S. patent application Ser. No. 11/914,606 (published Jan. 8, 2009, as Publication No. 2009-0011021 A1), U.S. patent application Ser. No. 12/300,951 (published Jul. 9, 2009, as Publication No. 2009-0175922 A1), U.S. patent application Ser. No. 13/192,276 (published Feb. 2, 2012, as Publication No. 2012-0027732 A1), U.S. patent application Ser. No. 13/383,796 (published May 10, 2012, as Publication No. 2012-0115222 A1), or are described in Roeder et al., *J. Biomech. Eng.*, vol. 124, pp. 214-222 (2002), in Pizzo et al., *J. Appl. Physiol.*, vol. 98, pp. 1-13 (2004), Fulzele et al., *Eur. J. Pharm. Sci.*, vol. 20, pp. 53-61 (2003), Griffey et al., *J. Biomed. Mater. Res.*, vol. 58, pp. 10-15 (2001), Hunt et al., *Am. J. Surg.*, vol. 114, pp. 302-307 (1967), and Schilling et al., *Surgery*, vol. 46, pp. 702-710 (1959), incorporated herein by reference.

In some embodiments, the physical property is density. In some embodiments, the physical property is stiffness. In other embodiments, the physical property is fibril orientation. In some embodiments, the physical property is collagen microstructure. In other embodiments, the physical property is porosity. In some embodiments, the physical property is the ratio of collagen type.

In certain embodiments, the composition comprises at least two regions. For example, the two or more regions can have different values of the physical property. In some embodiments, the values of the physical property of the two or more regions are present according to the gradient of the collagen compositions.

In some embodiments, at least one region comprises a high fibril density, and at least one other region comprises a low fibril density. For example, a high fibril volume fraction, or high density, could be from about 50% to about 100%, from about 60% to about 95%, from about 70% to about 93%, from about 80% to about 90%, from about 85% to about 95%, or from about 90% to about 100% and a low fibril density could be from about 5% to about 40%, from about 10% to about 30%, from about 15% to about 25%, or from about 20% to about 30%.

In other embodiments, at least one region comprises a high stiffness, and at least one other region comprises a low stiffness. For example, a high stiffness could be from about 0.5 MPa to about 2 MPa, from about 0.5 MPa to about 1.5 MPa, from about 0.7 MPa to about 1.5 MPa, from about 0.7 MPa to about 1.3 MPa, or from about 0.9 MPa to about 1.1 MPa and a low stiffness could be from about 0.01 MPa to about 0.4 MPa, from about 0.05 MPa to about 0.2 MPa, from about 0.05 MPa to about 0.1 MPa, or from about 0.08 to about 0.12 MPa.

In yet other embodiments, at least one region comprises a high porosity, and at least one other region comprises a low porosity. For example, a high porosity could be from about 50% to about 90%, from about 60% to about 85%, or from about 70% to about 80%, and a low porosity could be from about 1% to about 20%, from about 3% to about 10%, or from about 4% to about 6%.

In some embodiments, at least one region comprises an aligned fibril orientation, and at least one other region comprises a random fibril orientation.

In various embodiments, the composition further comprises cells. Any cell type within the knowledge of a person of ordinary skill in the art can be used with the compositions of the present disclosure. In some embodiments, the cells are stem cells. As used herein, "stem cell" refers to an unspecialized cell from an embryo, fetus, or adult that is capable of self-replication or self-renewal and can develop into a variety of specialized cell types (i.e., potency). The term as used herein, unless further specified, encompasses oligopotent cells (those cells that can differentiate into a few cell types, e.g., lymphoid or myeloid lineages), and unipotent cells (those cells that can differentiate into only one cell type). Hematopoietic stem cells may be isolated from, for example, bone marrow, circulating blood, or umbilical cord blood by methods well-known to those skilled in the art. A cell marker can be used to select and purify the hematopoietic stem cells. For example, suitable markers are the Lin−, Sca1+, and c-Kit+ mouse or Lin−, CD34+, and c-Kit+ human hematopoietic stem cell markers. Cell markers may be used alone or in combination to select and purify the desired cell type for use in the compositions and methods herein described. The collagen composition can be seeded with autogenous cells isolated from the patient to be treated. In an alternative embodiment the cells may be xenogeneic or allogeneic in nature.

In any of the embodiments described herein, the cells are seeded on the collagen composition at a cell density of about $1 \times 10^6$ to about $1 \times 10^8$ cells/ml, or at a density of about $1 \times 10^3$ to about $2 \times 10^6$ cells/ml. In one embodiment cells are seeded at a density of less than $5 \times 10^4$ cells/ml. In another embodiment cells are seeded at a density of less than $1 \times 10^4$ cells/ml. In another embodiment, cells are seeded at a density selected from a range of about $1 \times 10^2$ to about $5 \times 10^6$, about $0.3 \times 10^4$ to about $60 \times 10^4$ cells/ml, and about $0.5 \times 10^4$ to about $50 \times 10^4$ cells/ml. The cells are maintained, proliferated, or differentiated according to methods described herein or to methods well-known to the skilled artisan for cell culture.

In any of the various embodiments described herein, the collagen compositions of the present invention can be combined, prior to, during, or after polymerization, with nutrients, including minerals, amino acids, sugars, peptides, proteins, vitamins (such as ascorbic acid), or glycoproteins that facilitate hematopoietic stem cell culture, such as laminin and fibronectin, hyaluronic acid, or growth factors such as platelet-derived growth factor, or transforming growth factor beta, and glucocorticoids such as dexamethasone. In other illustrative embodiments, fibrillogenesis inhibitors, such as glycerol, glucose, or polyhydroxylated compounds can be added prior to or during polymerization. In accordance with one embodiment, cells can be added to the collagen or extracellular matrix components as the last step prior to the polymerization or after polymerization of the collagen compositions. In other illustrative embodiments, cross-linking agents, such as carbodiimides, aldehydes, lysl-oxidase, N-hydroxysuccinimide esters, imidoesters, hydrazides, and maleimides, and the like can be added before, during, or after polymerization.

In some embodiments, the composition is a hydrogel. Hydrogels are known to the skilled artisan. In some embodiments, the composition is a collagen-fibril matrix. A collagen-fibril matrix is known to the skilled artisan. In some embodiments, the composition is a porous matrix. A porous matrix is known to the skilled artisan.

In certain embodiments, the composition further comprises fluid. Although some fluid is removed from the collagen compositions pursuant to compression, an amount of fluid is retained in the compressed collagen compositions. In some embodiments, the percentage of fluid is present is between about 25% and about 99%. In some embodiments, the percentage of fluid is present is between about 45% and about 90%. In some embodiments, the percentage of fluid is present is between about 50% and about 80%. In some embodiments, the percentage of fluid is present is between about 50% and about 99%. In some embodiments, the percentage of fluid is present is between about 60% and about 70%.

In various embodiments, the composition is lyophilized. As used herein, the term "lyophilized" relates to the removal of water from a composition, typically by freeze-drying under a vacuum. However, lyophilization can be performed by any method known to the skilled artisan and the method is not limited to freeze-drying under a vacuum. Typically, the lyophilized composition is lyophilized to dryness, and in one embodiment the water content of the lyophilized composition is below detectable levels.

In another embodiment provided herein, a method of treating a patient is provided. The method comprises the step of implanting the engineered collagen composition of the present disclosure into the patient. Any of the embodiments of the engineered collagen compositions described herein can be utilized in the method of treating a patient.

In another embodiment provided herein, a method of manufacturing an engineered collagen composition is provided. The method comprises the step of compressing the collagen composition to form the gradient of at least one physical property. Any of the embodiments of the engineered collagen compositions described herein can be utilized in the method of manufacturing.

In some embodiments, the method of manufacturing comprises the step of polymerizing the collagen prior to compressing the collagen composition into a defined shape. In certain embodiments, the method of manufacturing comprises the step of tuning the physical property prior to compressing the collagen composition into a defined shape. As used herein, the term "tuning" refers to modification of the collagen composition under controlled conditions to obtain a desired physical property. For example, prior to compression, the collagen composition can be modified under controlled conditions to provide a desired value or quantity of one or more of the following physical properties: fibril density, pore size (fibril-fibril branching), elastic modulus, tensile strain, tensile stress, linear modulus, compressive modulus, loss modulus, fibril area fraction, fibril volume fraction, collagen concentration, cell seeding density, shear storage modulus (G' or elastic (solid-like) behavior), and phase angle delta (δ or the measure of the fluid (viscous)—to solid (elastic)—like behavior; δ equals 0° for Hookean solid and 90° for Newtonian fluid).

As a result of tuning the physical property prior to compressing the collagen composition, a high level interfibril association may be introduced to the collagen prior to compression of the compositions. This step allows for control of important mechanical properties prior to creation of the final compositions, and the controlled mechanical properties are retained following compression of the final compositions. Therefore, critical design features of collagen compositions can be optimized for purposes of predictably inducing desired cellular mechanisms in the collagen compositions.

In some embodiments, the compression is modulated through patterned fluid removal. Means of accomplishing patterned fluid removal of a composition are known to the skilled artisan. In other embodiments, the compression is modulated through patterned air removal. Means of accomplishing patterned air removal of a composition are known to the skilled artisan.

In various embodiments, the step of compressing removes fluid from the composition. Although some fluid is removed from the collagen compositions pursuant to compression, an amount of fluid can be retained in the compressed collagen compositions in some embodiments.

The collagen compositions described herein can be compressed into a number of different defined shapes. In some embodiments, the defined shape is a tube. In other embodiments, the defined shape is a sheet. In yet other embodiments, the defined shape is a sphere. In some embodiments, the defined shape is a slab. In other embodiments, the defined shape is a cylinder. In yet other embodiments, the defined shape is a cone.

In another embodiment, the methods, uses, and compositions described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

Example 1

Formation of Engineered Collagen Compositions Comprising a Gradient

This example demonstrates the formation of engineered collagen compositions comprising a gradient of a physical property. In this example, pig skin oligomer collagen was used as one source of collagen.

As shown in FIG. 1, collagen was polymerized at 5 mg/ml prior to loading in confined compression at 0.15% s−1 to a strain of 63%. The chamber used for polymerization and compression of the collagen composition was defined by closed boundary conditions on all sides with the exception of the platen, which represented porous polyethylene (50 μm pore size). During compression, the porous platen provides a controlled open boundary condition, allowing for fluid flow out of the construct.

Figure 2:
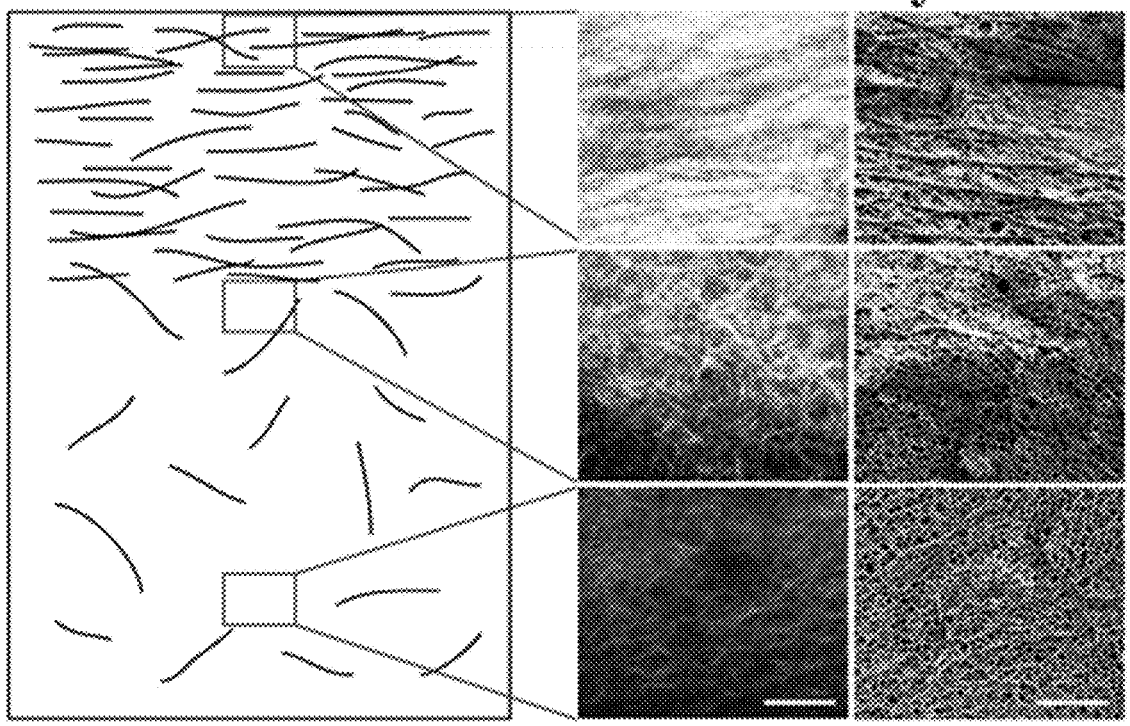
FIG. 2 shows a schematic demonstrating a compression-induced gradient formed within collagen oligomer construct with a gradient induced within the fibril microstructure confirmed using confocal reflection microscopy and cryo-SEM, and containing a scale bar equals 80 µm and 40 µm for confocal and cryo-SEM images, respectively.
Figure 3:
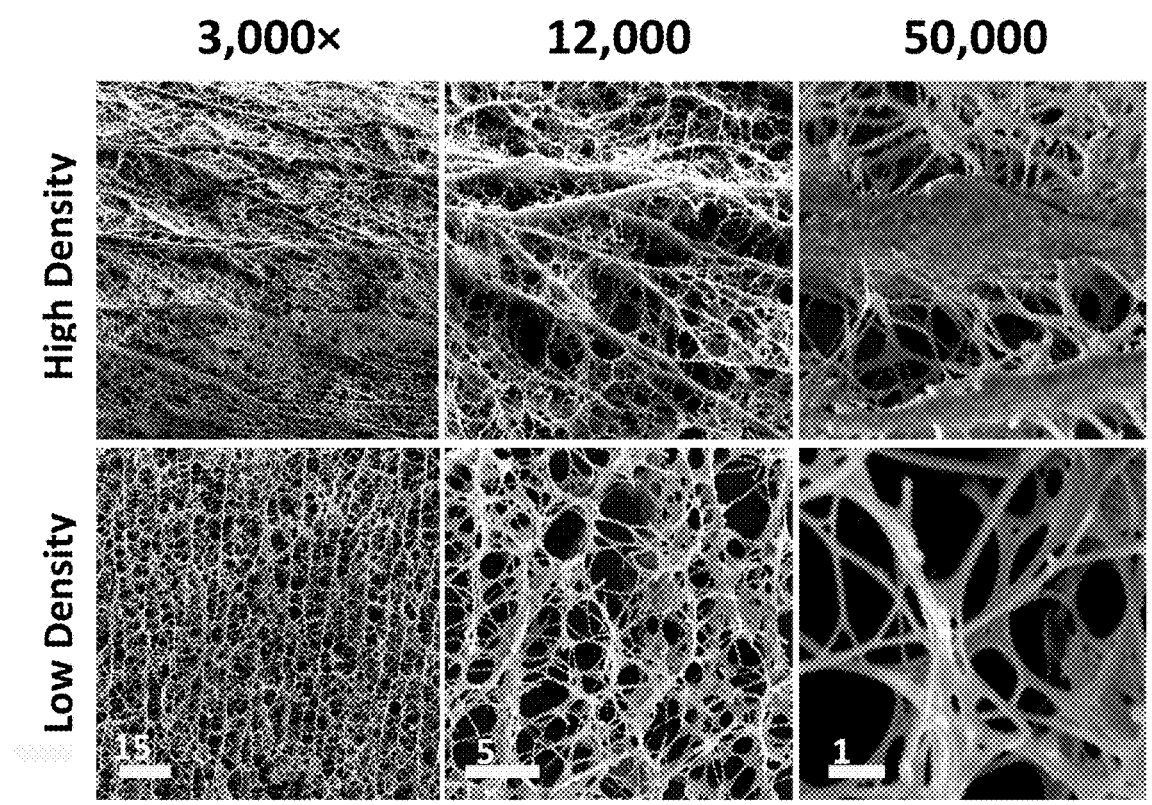
FIG. 3 shows the morphological changes caused by the densification process via scanning electron microscopy images of the collagen matrices over several magnifications. The high density regions result in fibril aggregates that are aligned in the horizontal direction. In comparison, the low density regions do not exhibit large fibril bundles or the aligned morphology.

The fibril microstructure of the collagen composition was determined along its height using confocal reflection microscopy. As shown in FIG. 1, a gradient was observed with densification and fibril alignment near the upper construct regions, progressing to a random homogenous, low-fibril density within the lower region of the construct. Corroborating data verifying the gradient was obtained using cryo-SEM. FIG. 2 shows that confocal (middle panel) and cryo-SEM (right panel) reveal collagen content and fibril organization, respectively, across sample depth of the collagen composition (left panel). FIG. 3 shows the high density region and low density region, respectively, of the collagen compositions.

Example 2

Formation of Engineered Collagen Compositions Comprising a Gradient

In this example, confined compression was investigated for the creation of gradient and high density collagen matrices. Type I oligomeric collagen was polymerized at 5 mg/mL. Matrices were then compressed in confined compression over a range of strain magnitudes (0, 50, 90%) and rates (0.1, 1.0, and 10%-s−1). Linear modulus and peak stress were measured during compression (n=8). Relative collagen density versus depth assessed via confocal microscopy (n=8). Fibril morphology was assessed via cryo-SEM (n=3).

Figure 4:
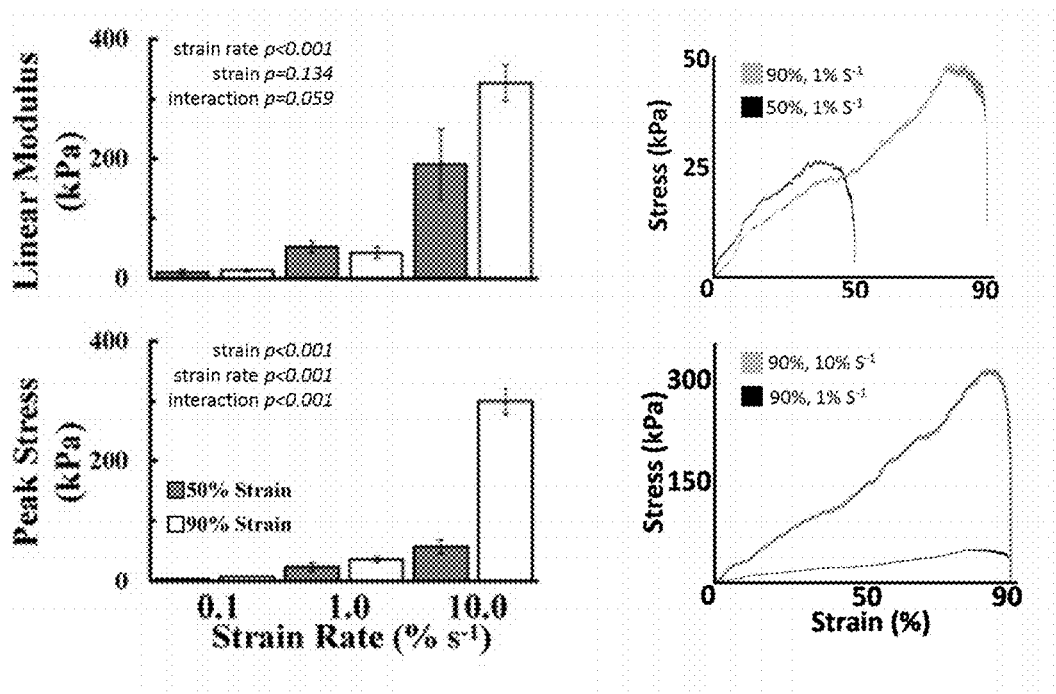
FIG. 4 shows quantitative differences between strain magnitude and strain rate on linear modulus and peak force during compression. Linear modulus (the slope of the line on the plots on the right side) is dependent on strain rate, but not strain magnitude. In contrast, peak stress (top of the curve on lower right) is seen to depend on both strain magnitude and strain rate.
Figure 5:
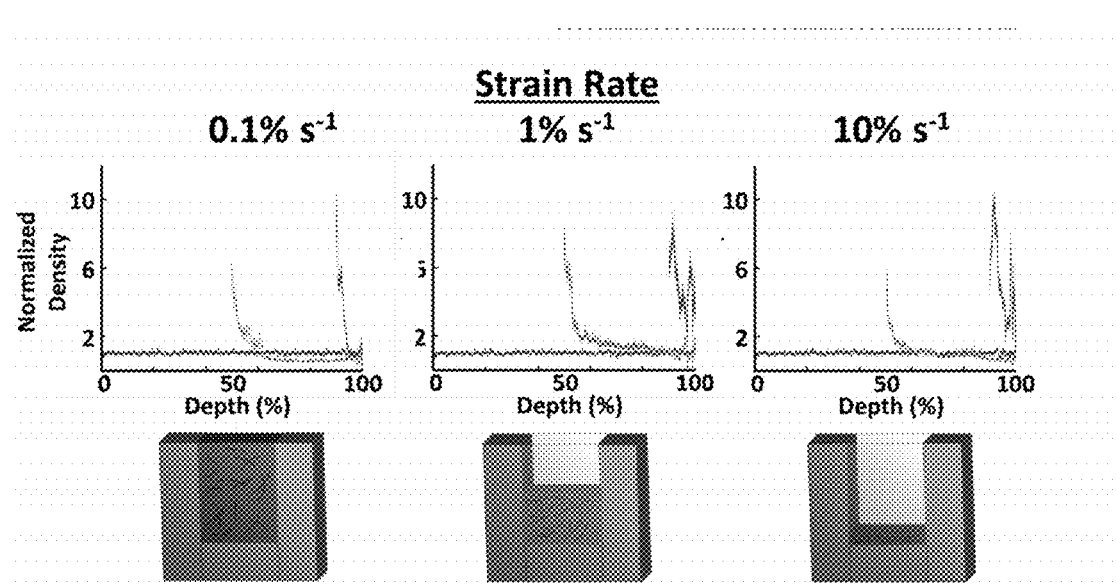
FIG. 5 shows the observed density effects at various strain rates. Regardless of strain rate (over two orders of magnitude from 0.1% $s^{-1}$ to 10% $s^{-1}$), high density collagen was observed at the top of the composition, with a gradient to low density collagen at the bottom of the composition.

During compression, linear modulus was dependent on strain rate (p<0.001) but not final strain magnitude (p=0.134). (see FIG. 4). Peak force was dependent on both strain magnitude (p<0.001) and rate (p<0.001). Confocal microscopy revealed that confined compression resulted in gradient collagen density with respect to depth (see FIG. 5). The highest concentrations (>7-fold) were observed at the impacted surface, decaying toward the initial density with depth into the matrix. SEM analysis revealed that high density regions exhibit highly aligned collagen fibrils orthogonal to the direction of compression, transitioning to random orientation in regions of lower (original) density. In conclusion, controlled densification as exemplified in this example allows the ability to approach physiological traits (i.e. density and fibril orientation) in gradients and near homogeneity, dependent on final strain magnitude.

Example 3

Design and Construction of Large-Scale, Adjustable Sample Mold and Compression Chamber In the instant example, a large-scale, adjustable sample mold and platen was fabricated. FIG. 6 shows the mold and platen. The sample was prepared in the mold and then subjected to confined compression. The mold is adjustable so that porous polyethylene is positioned as part of the platen and/or along the walls or bottom of the sample mold. The location of the porous polyethylene defines the resultant material physical gradient composition (see FIGS. 7A and 7B).

The instant procedure, which involves defined patterns of fluid flow from the collagen matrix, can be modulated to yield a variety of material physical gradient compositions. Factors defining the gradient of the collagen composition include: material chemical composition, initial material microstructure (architecture) and mechanical properties, mechanical loading mode (e.g., unconfined or confined compression, tension, shear), total mechanical strain, strain rate, interstitial fluid viscosity, platen porosity, and porous platen location.

Furthermore, the gradient induction process described herein can be applied to engineered collagen compositions prepared in the absence or presence of cells. The gradient induction can be applied to copolymer or multi-polymer materials, such as biomaterials and tissue constructs that contain various combinations of natural and/or synthetic polymers. The resulting engineered collagen composition with a desired gradient density has regions with different mechanical properties that will affect cell behavior.

The force of compression can come from any desired single direction in space, or from multiple directions at the same time generating various gradients. The shape of the starting composition may be defined by the beginning mold shape, and the resulting shape may be defined by the mold and the direction of applied compression. The resulting engineered collagen compositions may be maintained in a hydrated state or lyophilized to enhance long-term storage.

Example 4

Manufacture of Compressed Collagen Compositions

In this example, the collagen compositions were prepared oligomeric collagen derived from porcine skin as described previously (Kreger, S et al., "Polymerization and Matrix Physical Properties as Important Design Considerations for Soluble Collagen Formulations," *Biopolymers*, vol. 93, no. 8, pp. 690-707, August 2010). Briefly, oligomers were dissolved in hydrochloric acid and made aseptic by exposure to chloroform. Collagen matrices were prepared by diluting the collagen with 0.01N HCl and then neutralizing the mixture with a 10×PBS solution and 0.1N NaOH.

Collagen constructs were all created with the same starting collagen concentration (3.5 mg/mL) in 2 cm×4 cm block molds. After polymerization at 37° C. for 18 hours, a porous polyethylene platen (50 micron) was used to compress the blocks in the mold at a rate of 6 mm/min to a final thickness of 2 mm (1.6 mL). The final concentration of the collagen construct was controlled by varying the initial volume of 3.5 mg/mL collagen polymerized in the block mold, with 1.6 mL, 5.6 mL, and 11.2 mL of 3.5 mg/mL collagen being compressed to create the 3.5, 12.25, and 24.5 mg/mL, respectively.

Collagen constructs of 3.5, 12.25, and 24.5 mg/mL were prepared as described with one hour or 18 hour incubation times, and then punched into dogbone configurations with a gauge length of 26 mm, a gauge width of 4 mm, and a thickness of 2 mm. Hydrated samples were tested in tension to failure at a strain rate of 10 mm/second. n=7-10.

Figure 8A:
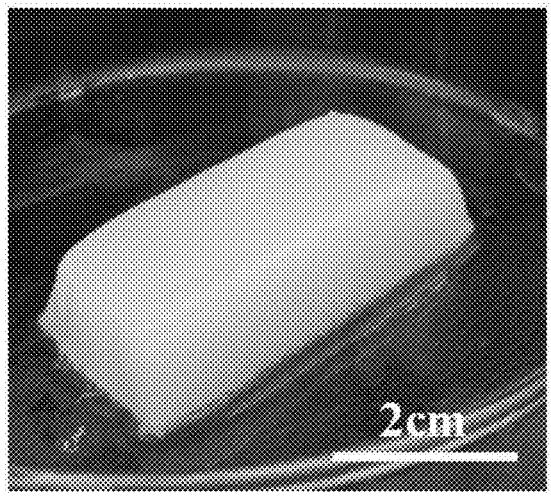
FIGS. 8A and 8B show (A) an uncompressed sample (14 mm thick) prepared from 3.5 mg/ml oligomer collagen and (B) a resultant collagen sheet (2 mm thick and approximately 24.5 mg/ml) following compression at 6 mm/min.
Figure 8B:
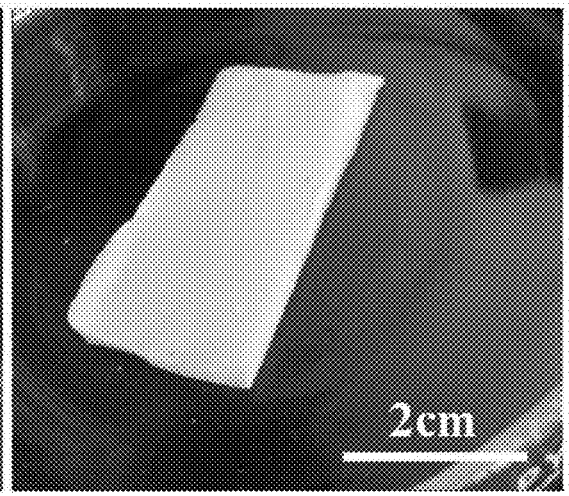

FIG. 8 shows engineered collagen compositions after polymerization to a thickness of 14 mm (left) and after confined compression to a thickness of 2 mm (right), showing the extent of confined compression.

Example 5

Analysis of Compressed Collagen Compositions

In order to examine the effect of compression on proteolytic degradation characteristics of the engineered collagen compositions, both the hydroxyproline (collagen) release and the change in compressive modulus due to collagenase treatment was observed. Engineered collagen compositions of 3.5, 12.25, and 24.5 mg/mL were punched into 2 mm thick cylinders with a diameter of 1 cm. Samples were then either tested in unconfined compression, or placed in a collagenase bath (5000 u/mL) for 2 hours and then tested. Unconfined compression was performed at 17%/second to 75% compression (n=7-8).

Samples of each collagen density were subjected to collagenase for 2 hours, and the amount of collagen degradation was measured on undigested samples and on samples after digestion using a spectrophotometric hydroxyproline assay (Sigma Aldrich). Constructs were stored in 100 uL of deionized water and then homogenized using concentrated HCl for use in the assay, as per the included protocol. (n=10-17)

Confocal and Cryo-SEM images of the microstructure were obtained. Cryo-SEM images of samples were obtained using an FEI NOVA nanoSEM 200. Statistical analysis was performed in Minitab statistical software using 2 sample T-tests assuming non-equal population variances.

Figure 9:
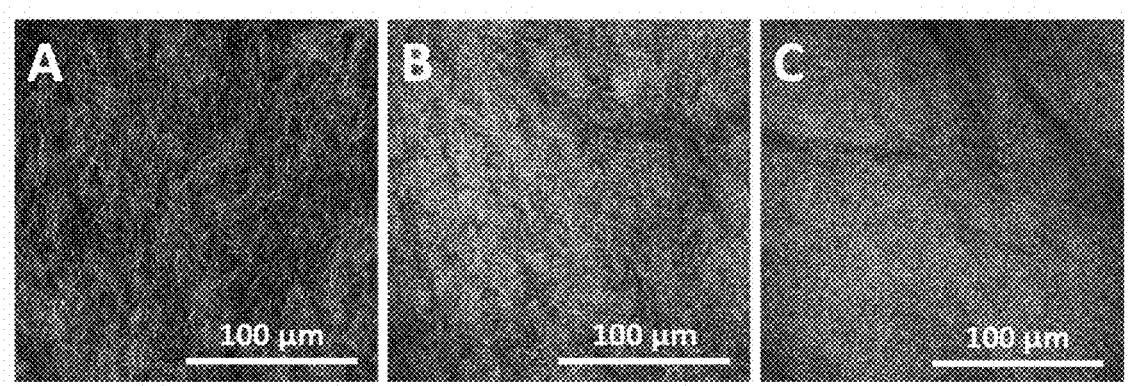
FIG. 9 shows confocal images (60×) of collagen compositions prepared at concentrations of 3.5 mg/mL (A), 12.25 mg/mL (B), and 24.5 mg/mL (C).
Figure 10:
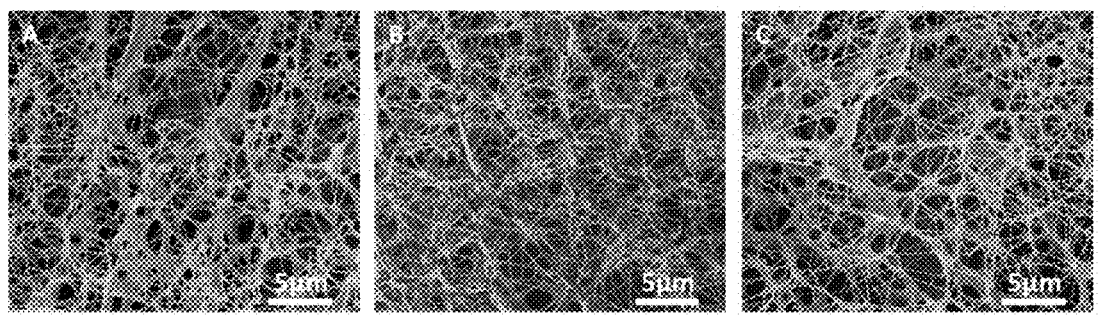
FIG. 10 shows Cryo-SEM images of 3.5 mg/mL (A), 12.25 mg/mL (B), and 24.5 mg/mL (C) collagen constructs. A progression of fibril density from lowest to highest is observed for 3.5 mg/ml, 12.25 mg/ml, and 24.5 mg/ml.

Both confocal imaging (see FIG. 9) and cryo-SEM imaging (see FIG. 10) showed fibrous structure at the micro scale. Under confocal imaging, the fibril density of the engineered collagen compositions could be seen to increase with increasing densification. In all cases the engineered collagen compositions retained a highly porous microstructure. In addition, the individual fibril size appeared unaffected.

Figure 11:
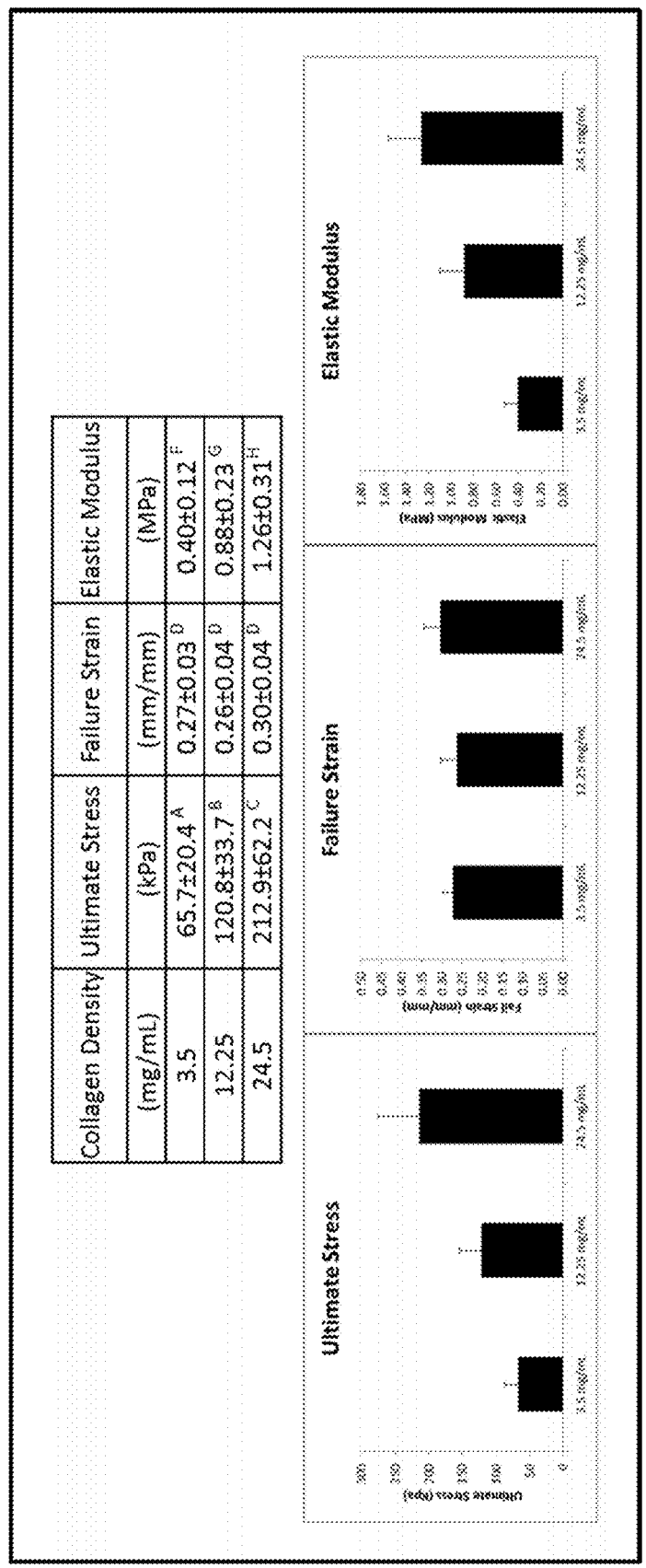
FIG. 11 shows the effect of compression on mechanical properties. Failure strain remained constant throughout the experimental groups, while both ultimate stress and elastic modulus increased nearly linearly with post-compression collagen concentration. Letters denote statistically significant groups ($p<0.05$). Plotted values represent mean±standard deviation.

All samples, regardless of concentration, failed near 0.27 mm/mm strain. The ultimate stress increased nearly linearly from 65.7 kPa to 120.8 kPa to 212.9 kPa in the 3.5, 12.25, and 24.5 mg/mL samples, respectively. The elastic modulus similarly increased across the sample groups, from 0.4 MPa in the base 3.5 mg/mL material, to 0.88 MPa in the 12.25 mg/mL group, and 1.26 MPa in the 24.5 mg/mL samples (n=7-10). Data are summarized in FIG. 11.

Figure 12:
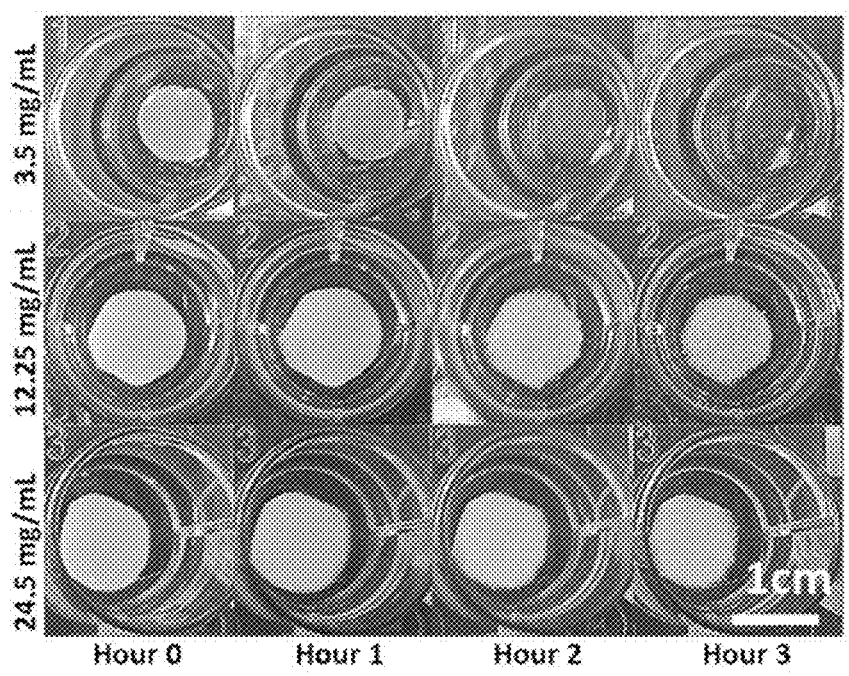
FIG. 12 shows a collagenase degradation analysis. Collagen compositions prepared at various concentrations are observed in wells of 31.2 U/mL collagenase, with each image representing a one hour time step.

Collagenase degradation of the samples showed visually different results over time, as seen in FIG. 12. Over the 3 hour time span, the 3.5 mg/mL sample appeared to be nearly entirely degraded, while the two more concentrated samples showed markedly better resistance to the collagenase. The 12.25 mg/mL sample developed pits throughout as the degradation went on. The 24.5 mg/mL sample only began to develop these regions much later in the degradation, and was concentrated to the edges of the construct.

Figure 13:
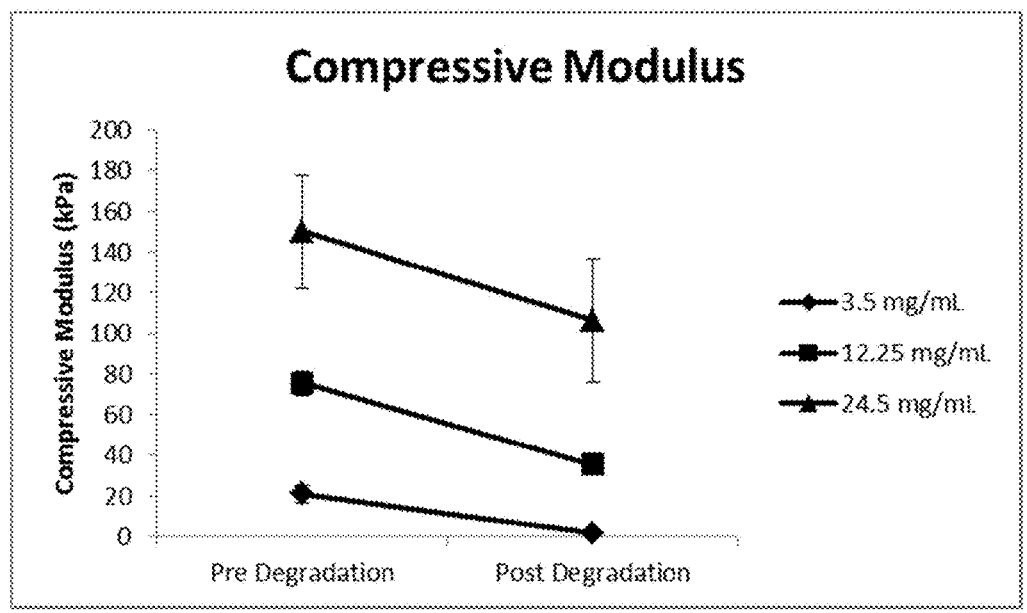
FIG. 13 shows the collagenase effect on compressive modulus. Pre- and post-degradation values of the compressive modulus are shown for uncompressed and compressed samples. Plotted values represent mean±standard deviation.

The compressive modulus for the samples was dramatically affected by the densification process, with the 3.5 mg/mL control sample having a compressive modulus of 21.0±4.3 kPa, the 12.25 mg/mL sample having a compressive modulus of 75.4±5.9 kPa, and the 24.5 mg/mL sample having a compressive modulus of 149.9±28.0 kPa. After digestion by collagenase, all samples showed reduced moduli of 1.4±0.7 kPa, 35.3±4.9 kPa, and 106.4±30.2 kPa compressive moduli for the 3.5, 12.25, and 24.5 mg/mL samples, respectively. Results are shown in FIG. 13.

Figure 14:
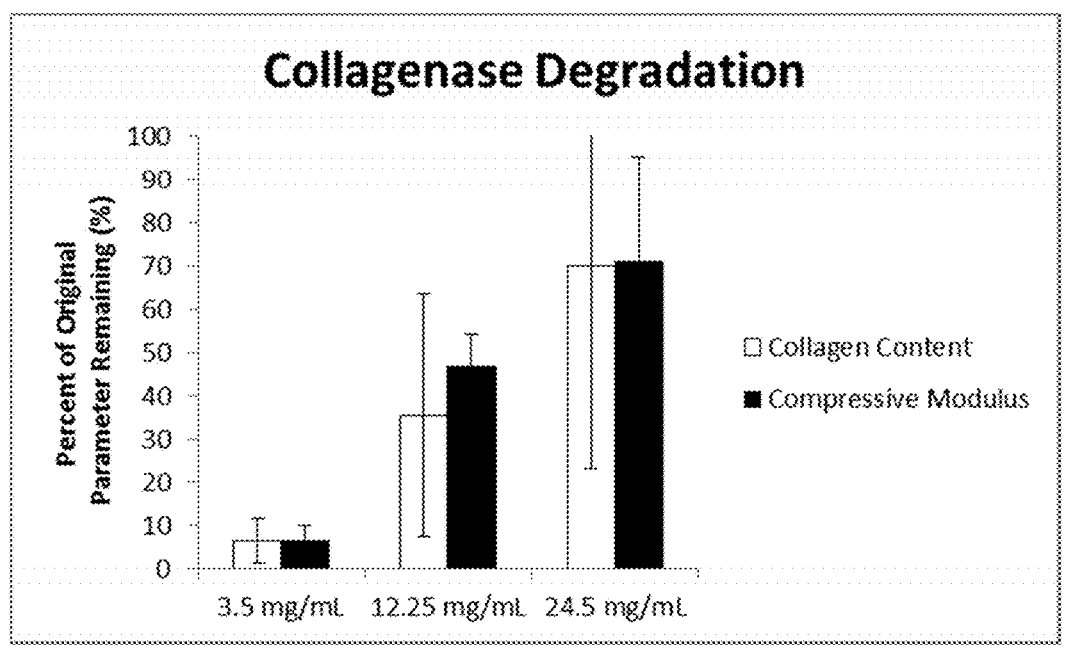
FIG. 14 shows a comparison of the effect of 2 hour collagenase degradation on compressive modulus and collagen (hydroxyproline) content of the samples. Each group showed statistically significant differences (p<0.05). Plotted values represent mean±standard deviation.

For compressive modulus and hydroxyproline (collagen) content studies, data after digestion in collagenase was correlated as percentage remaining compared to the values obtained for the undigested constructs. The compressive modulus of the constructs and the collagen content were similarly affected by digestion in collagenase, as seen in FIG. 14. With no densification, the 3.5 mg/mL sample group, after 2 hour digestion, 6.7±5.2% of the collagen was remaining in the sample, and 6.5±3.6% of the compressive modulus was found in the digested samples compared to the undigested controls. In the constructs densified to 12.25 mg/mL, 35.5±27.9% of the collagen content and 46.8±7.5% of the compressive modulus was remaining after the 2 hour digestion. In the constructs densified to 24.5 mg/mL, 70.0±46.7% of the collagen content and 71.0±24.1% of the compressive modulus was remaining after digestion. The data shows an increasing trend of remaining hydroxyproline (collagen) and compressive modulus after the set digestion time with increasing post-densification concentration.

Figure 15:
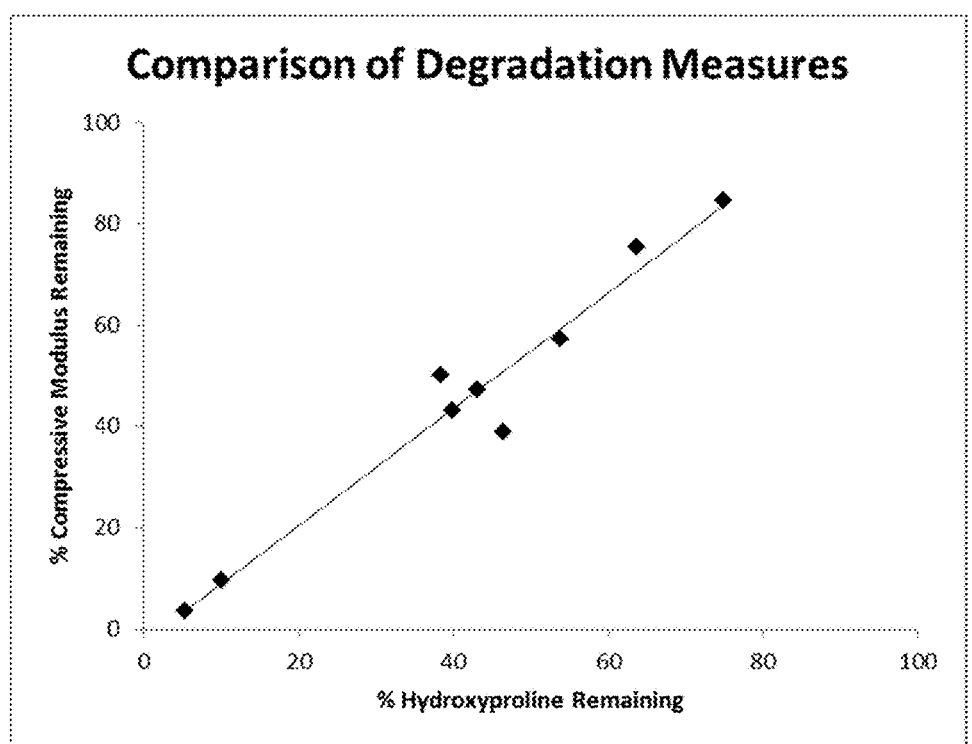
FIG. 15 shows a comparison of proteolytic degradation measures. As the percent hydroxyproline remaining is increased, the percent compressive modulus remaining is increased by a similar amount.

By plotting the percent hydroxyproline remaining vs percent compressive modulus remaining for individual samples, as seen in FIG. 15, a clear linear trend between the two measures of degradation can be observed. Both methods appear to be equally and identically descriptive of a sample's resistance to enzymatic degradation.

Densification of the engineered collagen compositions artificially increases the density by removing a portion of the fluid component. The new density of the engineered collagen compositions is directly related to the forced change in volume, where reducing the volume by half increases the collagen density (in mg/mL) by a factor of two. In this example, the density of the engineered collagen compositions was increased from a constant starting material by factors of 3.5× and 7×, effectively removing only a relatively small portion of the fluid matrix component. Similar studies performed by removing nearly the entire fluid component form atello collagen reduced the total volume to approximately 1/60th of its original value.

While typical collagen matrices made in labs are much less than 10 mg/mL, this study used a starting material of 3.5 mg/mL to create a scaffold with collagen content on the order of in vivo soft tissues.

The densification was shown to create significant differences in the mechanical strength of the material, with different extents of compression creating different mechanical strengths. The elastic modulus of the created materials greatly exceeds those of commercial collagen, and approaches those of soft tissues, as seen in Table 1.

TABLE 1

Material Properties - Tensile properties of commercial collagen, the created materials from this study, and other comparable biological tissues. All tissues are human unless otherwise indicated

| Material | Average Tensile Modulus (Mpa) |
| --- | --- |
| 2 mg/mL PureCol | 0.00205 |
| 4 mg/mL Sigma | 0.0573 |
| 4 mg/mL BD-RTC | 0.00144 |
| 3.5 mg/mL | 0.4 |
| 12.25 mg/mL | 0.88 |
| 24.5 mg/mL | 1.26 |
| Arteries and Veins | 0.6-3.5 |
| Sclera | 0.6-4.9 |
| Spinal Cord and Gray Matter | 0.4-3.6 |
| Patellar Articular Cartilage | 0.79 |
| Bovine Menisci | 0.41 |
| Dog Muscle - Along Fibers | 0.5 |
| Dog Muscle - Across Fibers | 0.79 |

Traditional collagen scaffolds utilizing exogenous crosslinks typically show, on the high end, an elastic modulus of 200-300 kPa when dry and ~15 kPa when wet, orders of magnitude weaker than the 200 kPa-1.2 MPa wet elastic modulus seen with this oligomeric collagen material without any exogenous crosslinks.

The densification also led to a change in the degradation profile of the material. Increasing the extent of densification led to a higher compressive modulus and higher collagen content remaining after equivalent degradation.

The material created through densification could be held and manipulated by hand without risk of falling apart under the strain. The material became visually more opaque with greater densification, as well as a mild increase in rigidity that could be felt by hand.

Example 6

Manufacture of Other Embodiments of Compressed Collagen Compositions

In this example, the collagen compositions were prepared from Type I collagen oligomers that were acid solubilized from the dermis of market weight pigs and lyophilized for storage as described previously (Kreger, S et al., "Polymerization and Matrix Physical Properties as Important Design Considerations for Soluble Collagen Formulations," *Biopolymers*, vol. 93, no. 8, pp. 690-707, August 2010). Prior to use, the lyophilized collagen was dissolved in 0.01 N HCl and rendered aseptic by exposure to chloroform at 4° C. Collagen oligomer solutions were diluted with 0.01 N HCl and neutralized with 10× phosphate buffered saline (PBS) and 0.1 N NaOH to achieve a neutral pH (7.4). Neutralized solutions were kept on ice prior to induction of polymerization by warming to 37° C.

Collagen-fibril constructs were created with an identical starting collagen concentration (3.5 mg/mL) in 2 cm×4 cm block molds. After polymerization and incubation at 37° C. for 18 hours, a porous polyethylene platen (pore size=50 μm) was used to compress the collagen-fibril construct in the mold at a rate of 6 mm/min to a final thickness of 2 mm (1.6 mL). The final concentration of the collagen-fibril constructs was controlled by varying the initial volume of collagen polymerized in the block mold, with 1.6 mL, 5.6 mL, and 11.2 mL of 3.5 mg/mL collagen (initial concentration) undergoing differential confined compression to create the 3.5, 12.25, and 24.5 mg/mL final concentration, respectively.

A subset of densified collagen-fiber constructs (24.5 mg/ml) were subjected to lyophilization and rehydration. Hydrated, densified samples were incubated in double-deionized water to remove excess salts before freezing in dry ice-ethanol bath. Samples were then lyophilized to dryness and stored in desiccated containers until use. Samples were rehydrated by incubating in double-deionized water for 1 hour.

Example 7

Preparation of Cellularized High-Density Collagen Compositions

To create cellularized, high-density collagen-fibril compositions, human adipose-derived stem cells (hASCs) were added to the collagen oligomer solution (3.5 mg/ml) and polymerized for 15 minutes at 37° C. Low passage hASCs were obtained and passaged 6-8 time. All cell media used was a 50/50 mixture of DMEM/F12 media with 10% FBS, 100 U/mL Penicillin, and 100 U/mL Streptomyosin.

Engineered collagen compositions representing different volumes, specifically 50 μL, 175 μL, or 350 μL, were created in Corning glass-bottom 96-well plate (Corning, N.Y.). To seed the hASCs into the constructs, cells were added as the final ingredient to the collagen mixture prior to polymerization. The collagen in the wells was densified to 50 μL final volume (1.5 mm final thickness) at 6 mm/min using a porous polyethylene platen. The cell density of the collagen compositions was $5 \times 10^5$ cells/mL after densification. Immediately following densification, 200 μL of media was added to the collagen compositions and media was changed after 48 hours. Cell viability was checked at 48 hours by staining with Celltracker (Molecular Probes, Eugene, Oreg.) and Propidium Iodide (Sigma-Aldrich). Actin and nuclear morphology were examined by fixing constructs at 48 hours with 3% paraformaldehyde and staining with Phalloidin (Molecular Probes, Eugene) and Draq5 (Biostatus Limited, Leicestershire, United Kingdom). (n=6-8).

Example 8

Biocompatibility Testing

To demonstrate biocompatibility of lyophilized, high-density collagen-fibril construct, circles were cut and placed in the bottom of a Corning 24-well plate (Corning, N.Y.). Biocompatible silicone rubber rings were used to hold the material on the plate bottom. hASCs ($1.25 \times 10^4$) were seeded on top of each construct. Tissue constructs were cultured in a humidified environment at 37° C. with 5% $CO_2$ in air. Media was changed after 24 hours, and the constructs were fixed using 3% paraformaldehyde after 48 hours. To investigate nuclear and actin morphology, the constructs were then stained using Draq5 (Biostatus Limited, Leicestershire, United Kingdom) and Phalloidin (Molecular Probes, Eugene, Oreg.) and imaged under confocal fluorescent microscopy.

Example 9

Fibril Microstructure Analysis

The fibril microstructure, of collagen constructs was visualized using confocal reflection microscopy and cryo-SEM. Confocal reflection microscopy was performed on an Olympus Fluoview FV-1000 confocal microscope using a 488 nm laser and reflected light was recorded to visualize the collagen fibrils. Image stacks were taken within the constructs over a depth of 50 μm with a depth step size of 2.5 μm using 488 nm and 633 nm lasers. For viability imaging, stacks of images were taken within the constructs over a depth of 100 μm with a depth step size of 5 μm. Cryo-SEM images of samples were obtained using an FEI NOVA nanoSEM 200. Briefly, samples were dehydrated via submersion in nitrogen cooled to its triple point. The nitrogen was then sublimated under vacuum for 20 minutes before sputter coating and imaging using an immersion secondary electron detector.

Both confocal and cryo-SEM imaging showed fibrous structures at the micro scale. Under confocal imaging, the fibril density of the structures could be seen to increase with increasing densification. In all cases the structure retained a highly porous microstructure. In addition, the individual fiber size was unaffected. In the lyophilized and rehydrated materials, the collagen fiber density was drastically increased, and the porous microstructure was retained.

Example 10

Tensile Testing

For tensile testing, all constructs cut into dog-bone configurations with a gauge length, width, of 26 mm, respectively. All densified constructs had a thickness of 4 mm, while those that were lyophilized and rehydrated had an approximate thickness of 0.4 mm. Similarly, the samples were tested in uniaxial tension to failure at a strain rate of 10 mm/second. (n=7).

All samples, regardless of concentration, failed near 0.28 mm/mm strain. The ultimate stress increased nearly linearly from 65.7 kPa to 120.8 kPa to 212.9 kPa in the 3.5, 12.25, and 24.5 mg/mL samples, respectively. The elastic modulus similarly increased across the sample groups, from 0.4 MPa in the base 3.5 mg/mL material, to 0.88 MPa in the 12.25 mg/mL group, and 1.26 MPa in the 24.5 mg/mL samples (n=7-10). Data are summarized in Table 2.

TABLE 2

Results of Tensile Tests

| Collagen Density (mg/mL) | Ultimate Stress (kPa) | Failure Strain (mm/mm) | Elastic Modulus (MPa) |
|---|---|---|---|
| 3.5 | 65.7 ± 20.4 A | 0.27 ± 0.03 D | 0.40 ± 0.12 F |
| 12.25 | 120.8 ± 33.7 B | 0.26 ± 0.04 D | 0.88 ± 0.23 G |
| 24.5 | 212.9 ± 62.2 C | 0.30 ± 0.04 D | 1.26 ± 0.31 H |

The lyophilized samples had a failure strain identical to the 24.5 mg/mL samples before lyophilization, at 0.30±0.04 mm/mm strain. The ultimate stress was greatly increased from 212.9±62.2 KPa before lyophilization to 2.11±0.56 MPa after lyophilization and rehydration. The elastic modulus was similarly affected, increasing from 1.26±0.31 MPa before lyophilization to 14.75±3.67 MPa after lyophilization. Data are summarized in Table 3.

TABLE 3

Results of Tensile Testing on Lyophilized and Rehydrated Materials

| Collagen Preparation | Collagen Concentration mg/mL | Volume mL | Ultimate Stress KPa | Failure Strain mm/mm | Elastic Modulus MPa |
|---|---|---|---|---|---|
| Base Material | 3.5 | 11.2 | 65.7 ± 20.4 | 0.27 ± 0.03 | 0.4 ± 0.12 |
| Post Densification | 24.5 | 1.6 | 212.9 ± 62.2 | 0.30 ± 0.04 | 1.26 ± 0.31 |
| Post Lyophilization and Rehydration | 122.5 | 0.32 | 2110 ± 560 | 0.30 ± 0.04 | 14.75 ± 3.67 |

The densification was shown to create significant differences in the mechanical strength or integrity of the material, with different extents of densification creating different mechanical strengths or elastic modulus and ultimate stress. The elastic modulus of the created materials greatly exceeds those of commercial collagen, and approaches those of soft tissues, as seen in Table 4. Traditional collagen scaffolds utilizing exogenous crosslinks typically show, on the high end, an elastic modulus of 200-300 kPa when dry and ~15 kPa when wet, orders of magnitude weaker than the 200 kPa-1.2 MPa wet elastic modulus seen with this oligomeric collagen material without any exogenous crosslinks.

TABLE 4

Tensile Properties of Materials

| Category | Material | Strain Rate | Average Tensile Modulus (Mpa) | REF |
|---|---|---|---|---|
| Commercial | 2 mg/mL PureCol | 35.7%/min | 0.00205 | 16 |
| Commercial | 4 mg/mL Sigma | 35.7%/min | 0.0573 | 16 |
| Commercial | 4 mg/mL BD-RTC | 35.7%/min | 0.00144 | 16 |
| Commercial | 4 mg/mL PSC | 35.7%/min | 0.277 | 16 |
| This Work | 3.5 mg/mL | 40%/sec | 0.40 | |
| This Work | 12.25 mg/mL | 40%/sec | 0.88 | |
| This Work | 24.5 mg/mL | 40%/sec | 1.26 | |
| Tissue | Arteries and Veins | Not Available | 0.6-3.5 | 23 |
| Tissue | Sclera | Not Available | 0.6-4.9 | 23 |
| Tissue | Spinal Cord and Gray Matter | Not Available | 0.4-3.6 | 23 |
| Tissue | Patellar Articular Cartilage | Not Available | 0.79 | 8 |
| Tissue | Bovine Menisci | Not Available | 0.41 | 8 |
| Tissue | Dog Muscle - Along Fibers | Not Available | 0.5 | 8 |
| Tissue | Dog Muscle - Across Fibers | Not Available | 0.79 | 8 |

Example 11

Suture Retention

Lyophilized and rehydrated samples were tested for suture retention strength. In accordance with ASTM standard protocol, 5-0 prolene suture was looped through the material at a "bite distance" (distance between the edge of the material and the suture) of 1.5 mm. The thickness of the samples was recorded using a micrometer. The suture was also looped through a hook connected to a tensile tester and tied using several square knots to prevent slipping. The suture was then pulled by the tensile tester at a crosshead speed of 25.4 mm/min until failure, and the peak force was recorded in grams. Samples of porcine aorta, bladder, pericardium, peritoneum, small intestine, and stomach were also tested. (n=4). Full thickness porcine dermis samples were also tested, however the sutures failed before being pulled through the tissue (data not shown).

The raw suture retention strength of the lyophilized and rehydrated collagen was 62.06±8.65 g. This was a similar scale to some of the tested tissues, such as the 100.48±42.22 g suture retention strength of the porcine stomach, and was far below other materials such as the 487.59±151.97 g suture retention strength of the aorta. However, due to the range of thicknesses of the different materials, a direct comparison between their retention strengths could not be directly made. The retention strengths were then normalized as retention strength in grams divided by the material thickness in mm. Through this normalization the lyophilized and rehydrated collagen performed higher than several of the porcine tissues, but much lower than pericardium. Data are presented in Table 5. Lyophilized collagen was found to have normalized suture retention strength per thickness statistically similar to porcine bladder, peritoneum, small intestine, and stomach tissues.

TABLE 5

Results of Suture Retention Testing

| Material | N | Thickness mm | Suture Retention Strength g | Statistical Groups | Normalized Retention Strength g/mm | Statistical Groups |
|---|---|---|---|---|---|---|
| Lyophilized Collagen | 5 | 0.4 | 62.06 ± 8.65 | A | 155.15 ± 21.64 | A |
| Aorta | 5 | 0.7 | 487.59 ± 151.97 | C | 696.55 ± 217.10 | B |
| Bladder | 5 | 2.5 | 303.18 ± 111.92 | BC | 121.27 ± 44.77 | A |
| Pericardium | 4 | 0.3 | 398.43 ± 149.67 | BC | 1328.11 ± 498.89 | C |
| Peritoneum | 4 | 0.8 | 242.69 ± 57.54 | AB | 303.36 ± 71.93 | AB |
| Small Intestine | 5 | 1 | 257.20 ± 108.41 | AB | 257.20 ± 108.41 | A |
| Stomach | 7 | 2.8 | 100.48 ± 42.22 | A | 35.89 ± 15.08 | A |

Extreme densification through lyophilization and rehydration resulted in the material being extensively stronger, with elastic modulus 2 orders of magnitude greater than the base collagen-fibril material. Its suture retention strength showed it to be comparable to multiple soft tissues, suggesting a good material for surgical use.

Example 12

Proteolytic Degradability

Samples of each collagen density were incubated in 1 mL of 31.2 U/mL collagenase for 2 hours, and the amount of collagen degradation was measured on undigested samples and on samples after digestion using a spectrophotometric hydroxyproline assay (Sigma Aldrich). Constructs were stored in 100 uL of deionized water and then homogenized using concentrated HCl for use in the assay, as per the included protocol. (n=10).

In order to examine the effect of densification on the proteolytic degradation characteristics of the scaffolds, the change in compressive modulus due to collagenase was observed. Collagen constructs of 3.5, 12.25, and 24.5 mg/mL were punched into 2 mm thick cylinders with a diameter of 1 cm. Samples were then either tested in unconfined compression, or incubated in 1 mL collagenase (31.2 U/mL) for 2 hours and then tested. Unconfined compression was performed at 17%/second to 75% compression and all samples were immersed in isotonic 1×PBS. (n=7).

Collagenase degradation of the samples showed visually different results over time. Over a 2 hour time span, the 3.5 mg/mL sample appeared to be nearly entirely degraded, while the two more concentrated samples showed markedly better resistance to the collagenase. The 12.25 mg/mL sample developed pits throughout as the degradation went on. The 24.5 mg/mL sample only began to develop these regions much later in the degradation, and was concentrated to the edges of the construct.

The compressive modulus for the samples was dramatically affected by the densification process, with the 3.5 mg/mL control sample having a compressive modulus of 21.0±4.3 kPa, the 12.25 mg/mL sample having a compressive modulus of 75.4±5.9 kPa, and the 24.5 mg/mL sample having a compressive modulus of 149.9±28.0 kPa. After digestion by collagenase, all samples showed reduced moduli of 1.4±0.7 kPa, 35.3±4.9 kPa, and 106.4±30.2 kPa compressive moduli for the 3.5, 12.25, and 24.5 mg/mL samples, respectively.

For compressive modulus and hydroxyproline (collagen) content studies, data after digestion in collagenase was correlated as percentage remaining compared to the values obtained for the undigested constructs. The compressive modulus of the constructs and the collagen content were similarly affected by digestion in collagenase. The data shows an increasing trend of remaining collagen and compressive modulus after the set digestion time with increasing post-densification concentration.

The densification led to a change in the proteolytic degradation profile of the material. Increasing the extent of densification led to a higher compressive modulus and higher hydroxyproline (collagen) content remaining after equivalent degradation.

Example 13

Cellular Response

Figure 16:
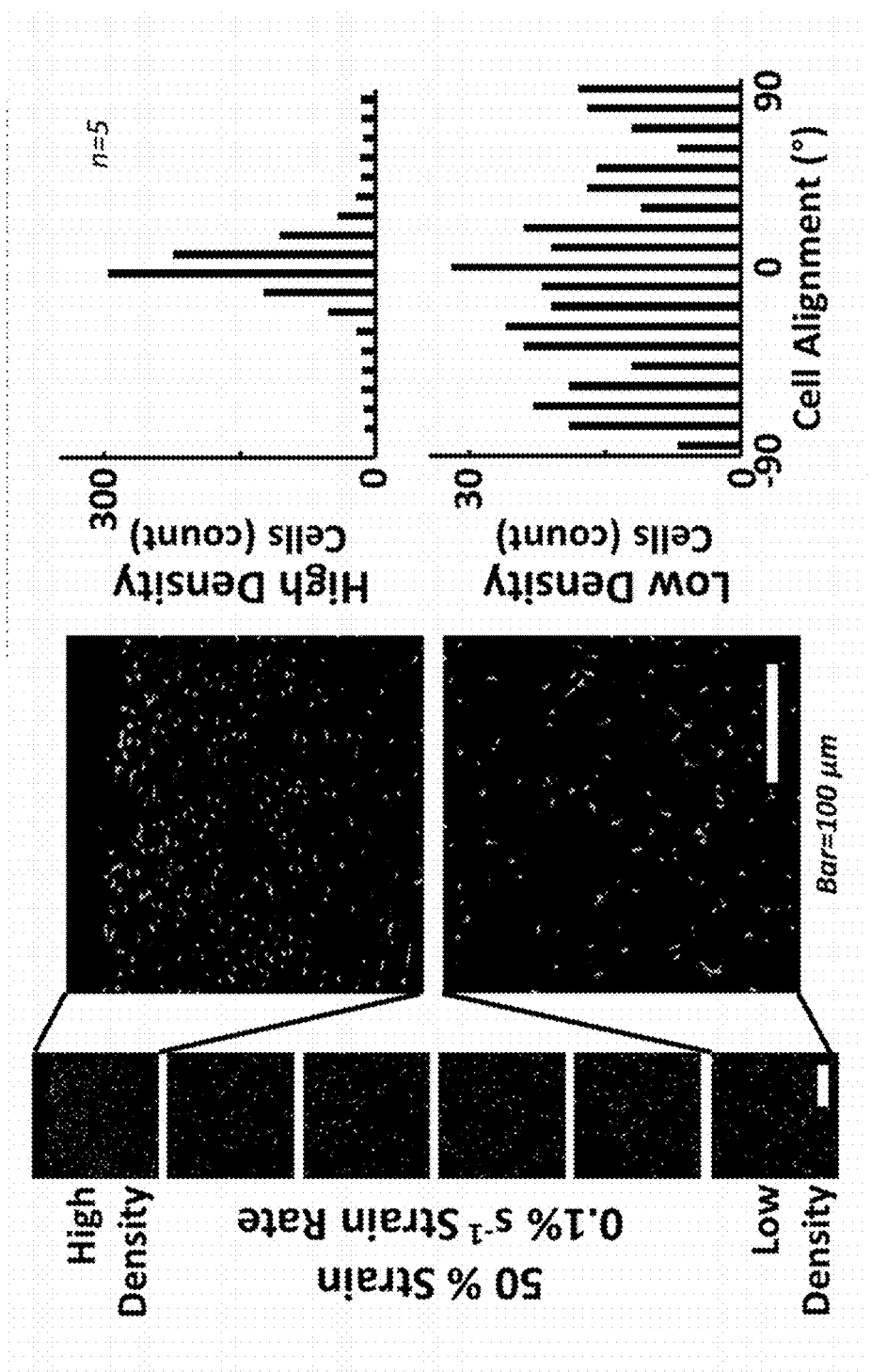
FIG. 16 shows that confined compression of collagen compositions results in heterogeneous collagen density, collagen fibril morphology, and local mechanical properties that have an effect on cellular morphology. After two days, cells encapsulated in the high density areas are elongated in the horizontal direction. The cells in the low density regions are not aligned in any particular direction (see histograms, which quantify cell elongation direction in high and low density regions, where 0 degrees is horizontal).

The cells seeded onto the lyophilized and rehydrated constructs exhibited spreading and attachment following the two days of incubation, with minimal signs of cell death as seen in FIG. 16. The cells formed a single culture layer on top of the collagen, and did not migrate through the construct over the incubation time.

The constructs seeded with hASCs prior to densification showed similar viability after 48 hours in culture. The undensified 3.5 mg/mL sample had 94.29±2.42% viable. The densified 12.25 and 24.5 mg/mL samples showed 89.57±2.43 and 88.96±2.48% viability, respectively. The densified samples were statistically different from the undensified sample at $\alpha=0.05$, but not statistically different from each other. Data are summarized in Table 6.

TABLE 6

48 Hour Viability Testing

| Collagen Concentration mg/mL | n | Viability % Live | Statistical Group |
|---|---|---|---|
| 3.5 | 8 | 94.29 ± 2.42 | A |
| 12.25 | 8 | 89.57 ± 2.43 | B |
| 24.5 | 6 | 88.96 ± 2.48 | B |

The collagen constructs seeded with hASCs showed markedly different morphology at the 3 different final collagen concentrations. In the control 3.5 mg/mL collagen, the cells spread widely and were randomly oriented throughout the construct. In the 12.25 mg/mL collagen, the cells were still highly elongated, but showed less spreading and a higher orientation towards the plane perpendicular to the direction of densification, although cells were still spread throughout the construct. In the 24.5 mg/mL, the cells showed very little elongation, instead taking on a more rounded morphology. These cells also showed preference to aligning along the plane perpendicular to the direction of densification.

Densification of collagen containing cells resulted in a statistically significant decrease in cell viability, however the percent viability only decreased by 5%. The total viability remained near 90% for the most densified sample, suggesting the densification process had little effect on the viability of the cells.

A change in collagen concentration through densification resulted in morphological changes in the hASCs. As the collagen concentration was increased, the cells were capable of less spreading, and, at the very high concentration, adopted a markedly different rounded morphology due to the increased concentration of collagen and resulting stiffness. This change in cell response due to changes of the extra-cellular matrix properties has been noted previously, although not to this collagen density. The rounded morphology seen at the 24.5 mg/mL collagen closely resembles the morphology of hASCs in vivo, suggesting an in vivo-like state of the highly densified collagen matrix.

Example 14

Formation of Collagen Composition Tubes

In this example, an engineered collagen composition can be formed in a tube shape using vacuum aspiration. Design features of initial collagen-fibril matrix, including extent of interfibril branching, proteolytic degradability, and intermolecular cross-link composition are controlled by varying ratios of collagen polymer building blocks (e.g., oligomer, telocollagen, atelocollagen) and polymerization conditions. Initial collagen-fibril matrix can be prepared in the presence and absence of various cell populations (e.g., smooth muscle cells, fibroblasts).

To form the tube, the rubber stopper end was removed from a syringe plunger and a hole was punched in it (biopsy punch). Then, a Polyethylene (PE) foam rod (longer than the length of the syringe or hollow tube) was inserted into the punched hole. Importantly, the PE foam rod should be flush with the pointed side of the plunger rubber, while the rest of the rod extends from the other side.

The plunger rubber was then inserted back into the syringe (the pointed side of the rubber should be closest to the tip of the syringe when fully inserted). Once fully inserted, there should be ~1 cm of PE rod sticking out of back end of the syringe (this will be where the vacuum is attached).

Then, neutralized collagen solution is injected into the syringe from top open end, ensuring minimal to no bubbles form. It is then placed in the incubator with syringe tip down, allowing polymerization to form a collagen-fibril matrix.

A vacuum is then attached to PE rod and fluid is carefully aspirated to compress collagen-fibril matrix to desired density. Using forceps, the densified collagen-fibril tube is carefully removed. The volume of initial collagen-fibril matrix, PE rod diameter, as well as rate and volume of fluid removal can be modulated so to achieve desired tube geometry and microstructure gradients within the densified collagen-fibril tube.

Figure 17:
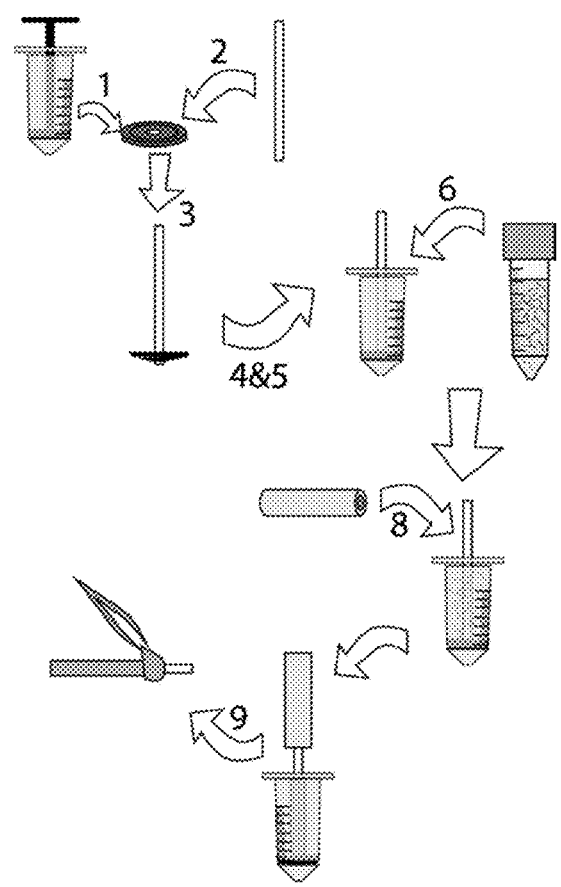
FIG. 17 shows the illustrative procedure of collagen-fibril tube formation using vacuum aspiration as the compression method.

The procedure of the instant example is shown in FIG. 17. In addition, FIGS. 18 and 19 show the densified collagen-fibril tube prepared by vacuum aspiration and after removal of the porous PE rod, respectively.

The invention claimed is:

1. An engineered collagen composition prepared by the process of:
polymerizing a solution of oligomeric collagen to form a mixture of solid collagen and fluid;
confining the mixture of solid collagen and fluid; and
compressing the mixture of solid collagen and fluid to form an engineered collagen composition.

2. The engineered collagen composition of claim 1, wherein the solution is non-acidic.

3. The engineered collagen composition of claim 1, wherein the compression of the mixture of solid collagen and fluid removes fluid from the mixture.

4. An engineered collagen composition prepared by the process of:
polymerizing a solution of oligomeric collagen to form a collagen-fibril construct;
confining the collagen-fibril construct; and
compressing the collagen-fibril construct to form an engineered collagen composition.

5. The engineered collagen composition of claim 4, wherein the solution is non-acidic.

6. The engineered collagen composition of claim 4, wherein the compression removes fluid from the collagen-fibril construct.

7. The engineered collagen composition of claim 4, wherein the confinement is in a container with one porous platen boundary.

8. The engineered collagen composition of claim 4, wherein the confinement is in a container with more than one porous platen boundary.

9. The engineered collagen composition of claim 4, wherein the engineered collagen composition possesses a gradient in at least one physical property.

10. The engineered collagen composition of claim 9, wherein the property is density.

11. The engineered collagen composition of claim 4, wherein the average density of collagen in the engineered collagen composition is greater than 3.5 mg/mL.

12. The engineered collagen composition of claim 4, wherein the percentage of fluid which remains after compression is between 25% and 99% of the original fluid composition.

13. The engineered composition of claim 12, wherein the percentage is between 50% and 80%.

14. The engineered composition of claim 4 in lyophilized form.

15. The engineered composition of claim 14, wherein the lyophilized form is rehydrated.

16. The engineered composition of claim 4, wherein the volume fraction of the fibrils in the engineered collagen composition is between about 1% to about 60%.

17. The engineered collagen composition of claim 4, wherein the elastic modulus is between 0.4 MPa and 1.26 MPa.

18. The engineered collagen composition of claim 4, wherein the compressive modulus is between about 17.0 kPa and about 178 kPa.

19. The engineered collagen composition of claim 4, wherein the wet elastic modulus is between about 200 kP and 1.2 MPa.

20. The composition of claim 4, wherein the compression is radial.

21. The engineered collagen composition of claim 4, wherein compression is done by vacuum aspiration.

22. The engineered collagen composition of claim 11, wherein the confinement is in a defined shape.

23. The engineered collagen composition of claim 12, wherein the defined shape is a cylinder.

24. The engineered collagen composition of claim 13, wherein the defined shape is selected from a tube, sheet, sphere, a slab, and a cone.

25. The engineered collagen composition of claim 4, wherein the elastic modulus is greater than 0.4 MPa.

26. The engineered collagen composition of claim 4, wherein the average density of collagen in the engineered collagen composition is between about 3 mg/ml and about 30 mg/ml.

27. The engineered collagen composition of claim 26, wherein the average density of collagen in the engineered collagen composition is about 3.5 mg/ml.

28. The engineered collagen composition of claim 26, wherein the average density of collagen in the engineered collagen composition is between about 4 mg/ml and about 10 mg/ml.

29. The engineered collagen composition of claim 26, wherein the average density of collagen in the engineered collagen composition is between about 10 mg/ml and about 20 mg/ml.

30. The engineered collagen composition of claim 26, wherein the average density of collagen in the engineered collagen composition is between about 20 mg/ml and about 30 mg/ml.

* * * * *